United States Patent [19]
Raeymaekers et al.

[11] Patent Number: 4,859,684
[45] Date of Patent: Aug. 22, 1989

[54] (1H-IMIDAZOL-1-YLMETHYL) SUBSTITUTED BENZIMIDAZOLE DERIVATIVES AND USE THEREOF IN TREATING ANDROGEN DEPENDENT DISORDERS

[75] Inventors: Alfons H. M. Raeymaekers, Beerse; Eddy J. E. Freyne, Rumst, both of Belgium; Gerard C. Sanz, Garges les Gonesse, France

[73] Assignee: Janssen Pharmaceutica N.V., Beerse, Belgium

[21] Appl. No.: 78,435

[22] Filed: Jul. 27, 1987

Related U.S. Application Data

[63] Continuation-in-part of Ser. No. 907,903, Sep. 15, 1986, abandoned.

[51] Int. Cl.⁴ .................. C07D 487/00; C07D 417/00; C07D 401/00; C07D 215/12

[52] U.S. Cl. ..................... 514/314; 548/327; 548/181; 546/167; 546/176; 546/271; 546/256; 514/365; 514/394; 514/395; 514/333; 514/338; 514/370

[58] Field of Search ............... 548/327, 181; 546/167, 546/176, 271, 256; 514/365, 394, 395, 314, 333, 338, 370

[56] References Cited

U.S. PATENT DOCUMENTS 4,198,516  4/1980  Merlo et al. ................... 548/327

*Primary Examiner*—Mary C. Lee
*Assistant Examiner*—Robert C. Whittenbaugh

[57] ABSTRACT

Novel (1H-imidazol-1-ylmethyl) substituted benzimidazole derivatives, compositions containing the same, and methods of treating androgen dependent disorders in mammals.

20 Claims, No Drawings

(1H-IMIDAZOL-1-YLMETHYL) SUBSTITUTED BENZIMIDAZOLE DERIVATIVES AND USE THEREOF IN TREATING ANDROGEN DEPENDENT DISORDERS

Cross-reference to related applications

This is a continuation-in-part of our co-pending application Ser. No. 907,903, filed Sept. 15, 1986 now abandoned.

BACKGROUND OF THE INVENTION:

A large number of imidazole derivatives are known in the art as anti-fungal agents. Recently ketoconazole, an orally active imidazole derivative with a broad-spectrum activity against a variety of yeasts, dermatophytes and dimorphous fungi, has been reported to inhibit steroid synthesis in Annals of Internal Medicine, 97, 370 (1982).

In U.S. Pat. No. 4,410,539 there are described a number of (1H-imidazol-1-ylmethyl) substituted indole derivatives which compounds are useful as thromboxane synthetase inhibitors.

Further there are described in U.S. Pat. No. 4,335,132 a number of pyridyl substituted 2-hydroxy or mercapto benzimidazole derivatives which are useful as cardiotonic agents.

The compounds of the present invention differ therefrom by the fact that they contain a benzimidazole moiety which is invariably substituted with 1H-imidazol-1-ylmethyl radical and by their effective inhibition of the androgenic hormone biosynthesis. The compounds of the present invention are therefore useful in preventing or therapeutically treating androgenic hormone dependent disorders in mammals.

DESCRIPTION OF THE PREFERRED EMBODIMENTS

The present invention is concerned with imidazole derivatives of formula

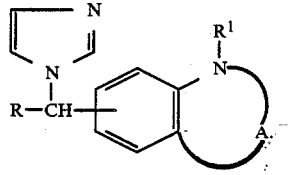

the pharmaceutically acceptable acid addition, metal or amine substitution salts and the stereochemically isomeric forms thereof, wherein R is hydrogen; $C_{1-10}$alkyl; $C_{3-7}$cycloalkyl; $Ar^1$ or $Ar^1$-$C_{1-6}$alkyl;

$R^1$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;

A is a bivalent radical having the formula

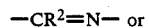 (a)

 (b)

wherein the carbon atom in the bivalent radical (a) or (b) is connected to —$NR^1$;

said $R^2$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl or hydroxy; $C_{1-10}$alkyloxy; $C_{1-6}$alkyloxy substituted with $Ar^1$ or $C_{3-7}$cycloalkyl; $C_{3-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl or $Ar^1$—(CHOH)—;

said X being O or S;

said $R^3$ being hydrogen, $C_{1-6}$alkyl or $Ar^2$-$C_{1-6}$alkyl;

$Ar^1$ is phenyl, substituted phenyl, pyridinyl, aminopyridinyl, imidazolyl, thienyl, halothienyl, furanyl, halofuranyl or thiazolyl;

$Ar^2$ is phenyl or substituted phenyl;

in $Ar^1$ and $Ar^2$ said substituted phenyl being phenyl substituted with 1, 2 or 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

As used in the foregoing definitions the term halo is generic to fluoro, chloro, bromo and iodo; the term "$C_{1-4}$alkyl" is meant to include straight and branch chained saturated hydrocarbon radicals having from 1 to 4 carbon atoms such as, for example, methyl, ethyl, 1-methylethyl, 1,1-dimethylethyl, propyl, 2-methylpropyl, butyl and the like; $C_{1-6}$alkyl and $C_{1-10}$alkyl include $C_{1-4}$alkyl radicals and the higher homologs thereof having respectively 6 to 10 carbon atoms; the term "$C_{3-7}$cycloalkyl" is generic to cyclopropyl, cyclobutyl, cyclopentyl, cyclohexyl and cycloheptyl. "$C_{3-6}$alkenyl" is meant to include straight and branch chained hydrocarbon radicals containing one double bond and having from 3 to 6 carbon atoms such as, for example, 3-propenyl, 2-butenyl and the like; "$C_{3-6}$alkynyl" is meant to include straight and branch chained hydrocarbon radicals containing one triple bond and having from 3 to 6 carbon atoms such as, for example, 3-propynyl, 2-butynyl and the like; provided that when the said $C_{3-6}$alkenyl or $C_{3-6}$alkynyl is substituted on a heteroatom then the carbon atom of said $C_{3-6}$alkenyl or $C_{3-6}$alkynyl connected to said heteroatom is saturated.

It is to be understood that the 1H-imidazol-1-ylmethyl moiety may be substituted on either the 4,5,6 or 7 position of the benzimidazole heterocyclic ring. In addition, the compounds of formula (I) may also contain in their structure a tautomeric system and consequently these compounds can be present in each of their tautomeric forms. Also within the scope of the invention are the compounds of formula (I) in the form of hydrates or in solvent addition forms.

Preferred compounds within the present invention are those compounds of formula (I) wherein A is a bivalent radical of formula (a); $R^1$ is hydrogen; $C_{3-7}$cycloalkyl; $Ar^2$; $C_{1-10}$alkyl; $C_{1-6}$alkyl substituted with $Ar^1$ or $C_{3-7}$cycloalkyl; hydroxy or $C_{1-6}$alkyloxy; and $R^2$ is hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, quinolinyl or indolinyl; $C_{1-6}$alkyloxy; $C_{3-6}$alkenyl substituted with $Ar^1$; or $Ar^2$-carbonyl.

Particularly preferred compounds within the present invention are those preferred compounds wherein the 1H-imidazol-1-ylmethyl moiety is substituted on either the 5 or 6 position of the benzimidazole ring; R is hydrogen; $C_{1-6}$alkyl or $Ar^1$; $R^1$ is hydrogen; $C_{1-6}$alkyl or $Ar^2-C_{1-6}alkyl$; and $R^2$ is hydrogen; di- or trihalomethyl; $C_{1-6}alkyl$ substituted with $Ar^1$, quinolinyl or indolinyl; $C_{1-10}alkyl$; $Ar^1$; $C_{1-6}alkyloxy$ or $Ar^2$-carbonyl.

Especially preferred compounds within the present invention are those particularly preferred compounds wherein R is $C_{1-6}alkyl$ or $Ar^2$; $R^1$ is hydrogen; and $R^2$ is hydrogen, $C_{1-6}alkyl$ or $Ar^1$.

The most preferred novel compounds within the invention are selected from the group consisting of 5-[(1H-imidazol-1-yl)phenylmethyl]-2-methyl-1H-benzimidazole and 5-[(3-chlorophenyl)(1H-imidazol-1-yl)methyl]-1H-benzimidazole the pharmaceutically acceptable acid addition salts and the stereochemically isomeric forms thereof.

The compounds of formula (I) can generally be prepared by N-alkylating 1H-imidazole (III), an alkali metal salt or a $triC_{1-6}alkyl$ silyl derivative thereof, with a benzimidazole of formula (II).

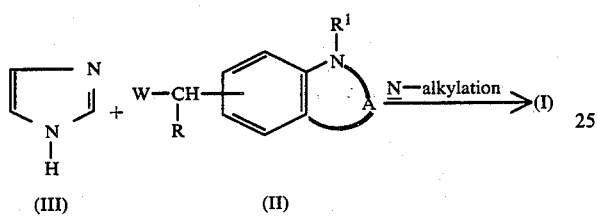

(III)  (II)

W as used in the foregoing and following reaction schemes is an appropriate leaving group such as, for example, halo, e.g., chloro, bromo or iodo, a sulfonyloxy group, e.g. methylsulfonyloxy or 4-methylphenylsulfonyloxy, and where W is connected to a —C(=X)— radical it may also be $C_{1-6}alkyloxy$, $C_{1-6}alkylthio$, aryloxy or arylthio.

The above described N-alkylation is conveniently carried out by stirring the reactants in the presence of a suitable organic solvent such as, for example, an aromatic hydrocarbon, e.g., benzene, methylbenzene, dimethylbenzene, and the like; a ketonoe, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), nitrobenzene, dimethyl sulfoxide (DMSO), 1,3-dimethyl-3,4,5,6-tetrahydro-2(1H)-pyrimidinone (DMPU), 1,3-dimethyl-2-imidazolidinone (DMEU), 1-methyl-2-pyrrolidinone, acetonitrile, hexamethylphosphor triamide (HMPT), benzonitrile and the like; and mixture of such solvents. Somewhat elevated temperatures may be appropriate to enhance the rate of the reaction and preferably the reactoin is carried out at the reflux temperature of the reaction mixture. In order to enhance the reaction rate it may be advantageous to use an excess of imidazole or to add to the reaction mixture an appropriate base such as, for example, an alkali metal carbonate or hydrogen carbonate, sodium hydride or an organic base such as, for example, N,N-diethylethanamine, N-(1-methylethyl)-2-propanamine and the like.

In some cases it may be advantageous to first convert 1H-imidazole (III) to its alkalimetal salt form or to a $triC_{1-6}alkyl$ silyl derivative thereof and subsequently react said salt form or silyl derivative with the benzimidazole derivative of formula (II). The said salt form can conveniently be prepared by reacting 1H-imidazole with and alkalimetal base such as, for example, an alkali metal hydroxy, alkoxide or hydride. The said $triC_{1-6}al$-kyl silyl derivative of 1H-imidazole can in turn be prepared by reacting imidazole with for example a trialkyl halo silane.

Compounds of formula (I) may also be prepared by reacting an intermediate of formula (IV) with 1,1'-carbonylbis[1H-imidazole].

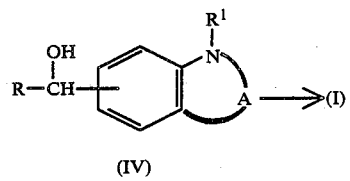

(IV)

In some instances the reaction of (IV) with 1,1'-carbonylbis[1H-imidazole] first yields an intermediate of formula (V) which may in situ or, if desired, after isolating and further purifying it, be converted to the desired compounds of formula (I).

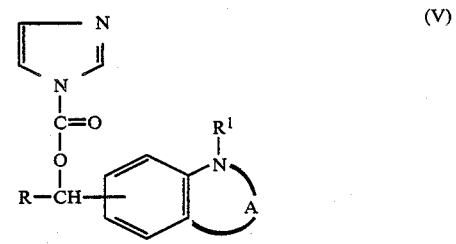

(V)

Said reaction may conveniently be conducted in a suitable solvent such as, for example, an ether, e.g., 1,4-dioxane, tetrahydrofuran; a halogenated hydrocarbon, e.g., di- or trichloromethane; a hydrocarbon, e.g., benzene, methylbenzene; a ketone, e.g., 2-propanone, 4-methyl-2-pentanone, N,N-dimethylformamide, N,N-dimethylacetamide, or mixtures of such solvents. In order to enhance the reaction rate, it may be advantageous to heat the reaction mixture, preferably to the reflux temperature of the reaction mixture.

The compounds of formula (I) can alternatively be prepared under similar conditions as are described in the literature for the preparation of benzimidazoles starting from benzenediamines or 2-nitrobenzenamines. Depending on the nature of —A— in the compounds of formula (I) to be prepared, the following procedures may, for example, be utilized.

The compounds of formula (I), wherein —A— is a bivalent radical of formula (a) and $R^1$ is hydrogen, $C_{3-7}$-cycloalkyl, $Ar^2$, $C_{1-10}alkyl$ or $C_{1-6}alkyl$ substituted with $Ar^1$ or $C_{3-7}$cycloalkyl, said compounds being represented by formula (I-a) and said $R^1$ being represented by formula $R^{1-a}$, can be prepared by reacting a 1,2-benzenediamine of formula (VI) with a carboxylic acid of formula (VII) or a functional derivative thereof.

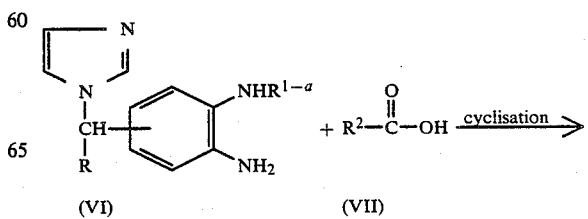

(VI)  (VII)

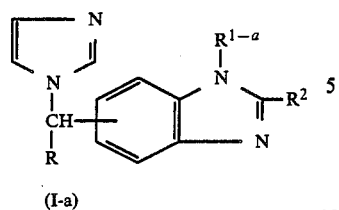

(I-a)

Said functional derivative of (VII) is meant to comprise the halide, anhydride, amide, and ester form of (VII), including the ortho and imino ester form thereof.

Said functional derivative may be generated in situ or, if desired, be first isolated and further purified before reacting it with the 1,2-benzenediamine of formula (VI). The cyclisation reaction of (VI) and (VII) is preferably carried out in an aqueous solution of a mineral acid, such as, for example hydrochloric acid, hydrobromic acid, sulfuric acid and the like. However solvents such as, for example, an alcohol, e.g., methanol, ethanol, 2-propanol, 1-butanol; a halogenated hydrocarbon, e.g., trichloromethane, dichloromethane, and mixtures of such solvents with water may be employed. In some instances an excess of a carboxylic acid of formula (VII) or the corresponding alkyl ester may be used as a solvent. Elevated temperatures and stirring may enhance the reaction rate.

In the instance where (VII) is an acid or the corresponding alkyl ester thereof, the cyclisation reaction of (VI) and (VII) may be conducted in the presence of a suitable dehydrating agent such as, for example, polyphosphoric acid, phosphorous pentoxide and the like.

In a preferred method of conducting the above cyclisation reaction there is used the imino ester form of (VII). The desired compounds of formula (I-a) are then easily prepared by stirring at room temperature or at an elevated temperature in an acidic medium such as, for example, acetic acid, or a lower alkanol, whereto an appropriate acid, e.g., hydrochloric acid has been added. When the imino ester is in the form of an acid addition salt there is no need for adding additional acid.

In the instance where (VII) is an ortho ester, said cyclisation reaction of (VI) and (VII) may be carried out in the prsence of a carboxylic acid such as, for example, formic acid, acetic acid and the like, and, if desired, in the presence of a suitable solvent such as, for example, an alcohol, e.g., methanol, ethanol, 2-propanol, a halogenated hydrocarbon, e.g., trichloromethane, dichloromethane and the like, and mixtures of such solvents.

In some instances the reaction of (VI) with (VII) first yields an intermediate of formula (VIII) which may in situ or, if desired, after isolating and purifying it, be cyclized by heating or stirring it in the presence of an acid, such as, for example, a mineral acid, e.g., hydrochloric acid or a carboxylic acid, e.g., formic acid and the like.

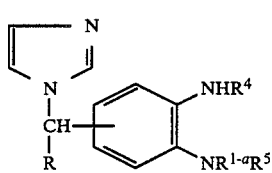

(VIII)

In (VIII) one of the radicals $R^4$ or $R^5$, represents a hydrogen or a

group and the other represents a

group.

The compounds of formula (I-a) can also be prepared by condensing a 1,2-benzenediamine of formula (VI) with an aldehyde of formula (IX), or optionally an addition product thereof with an alkali metal hydrogen sulfite.

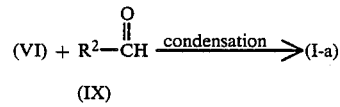

In some instances the reaction of (VI) with (IX) first yields an intermediate of formula (X) which may in situ or, if desired, after isolating and further purifying it, be cyclized to the desired compounds of formula (I-a).

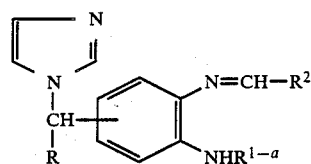

The condensation reaction of (VI) with (IX) may be conducted in a suitable solvent, such as, for example; water; an alcohol e.g., methanol, ethanol, 2-propanol, 1-butanol; a halogenated hydrocarbon, e.g., trichloromethane, dichloromethane; a hydrocarbon e.g., benzene, hexane and the like, and mixtures of such solvents, if desired, in the presence of an acid, e.g., hydrochloric acid, hydrobromic acid, formic acid, acetic acid, propanoic acid and the like. There may be added to the reaction mixture an appropriate oxidizing agent such as, for example, nitrobenzene, mercuric oxide, Cu(II) and Pb(II) salts or other suitable oxidants known in the art, or the aldehyde itself, when added in excess, may serve as an oxidant. Somewhat elevated temperatures and stirring may enhance the rate of the reaction.

The compounds of formula (I-a) may also be prepared by reductively cyclizing an intermediate of formula (XI) in a suitable solvent such as, for example, t-butylbenzene with an appropriate reductant such as, for example triethylphosphite, thus preparing compounds of formula (I-a) wherein $R^{1-a}$ is hydrogen, said compounds being represented by formula (I-a-1), and if further desired, reacting the compounds of formula (I-a-1) with a reagent W-$R^{1-a-1}$, (XII), thus preparing compounds of formula (I-a) wherein $R^{1-a}$ is other than hydrogen, said compounds being represented by the formula (I-a-2).

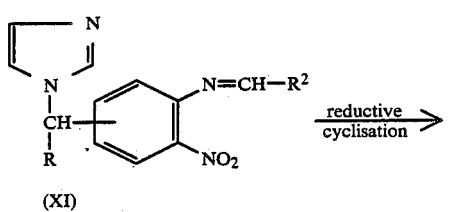

(XI)

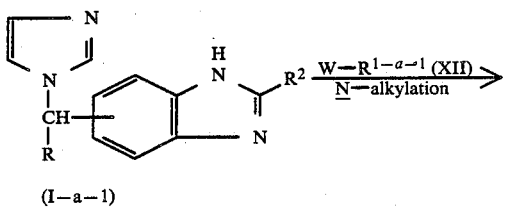

(I—a—1)

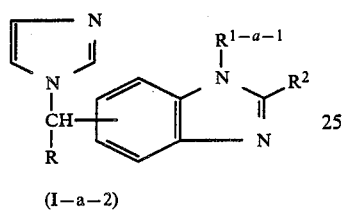

(I—a—2)

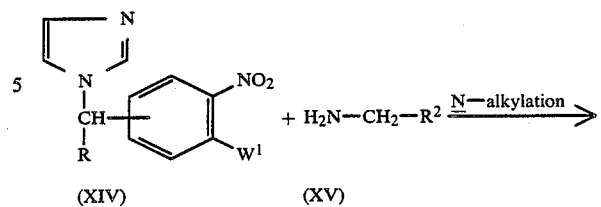

(XIV)    (XV)

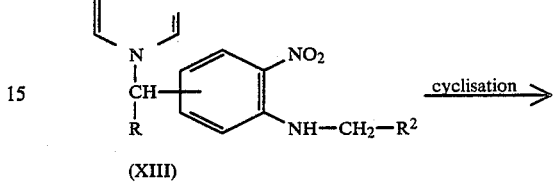

(XIII)

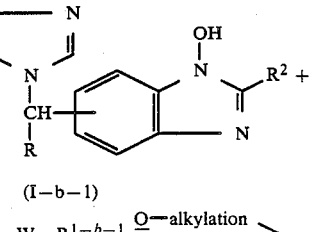

(I—b—1)

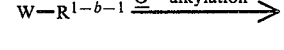

(XVI)

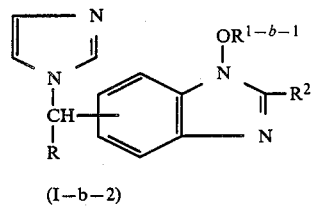

(I—b—2)

In (XII) W has the previously defined meanings and $R^{1-a-1}$ is $C_{3-7}$cycloalkyl, $Ar^2$, $C_{1-10}$alkyl or $C_{1-6}$alkyl substituted with $Ar^1$ or $C_{3-7}$cycloalkyl.

Said N-alkylation reaction is conveniently conducted in an inert organic solvent such as, for example, a hydrocarbon, e.g., methylbenzene, dimethylbenzene; an alkanol, e.g., methanol, ethanol; a ketone, e.g., 4-methyl-2-pentanone; an ether, e.g., 1,4-dioxane, tetrahydrofuran; N,N-dimethylformamide (DMF); N,N-dimethylacetamide (DMA). The addition of a base such as, for example, an alkali or an earth alkaline metal carbonate, hydrogen carbonate or hydroxide, or an organic base, such as, for example, a tertiary amine, may be utilized to pick up the acid which is liberated during the course of the reaction. Somewhat elevated temperatures may enhance the rate of the reaction.

The compounds of formula (I), wherein —A— is a bivalent radical of formula (a) and $R^1$ is hydroxy, said compounds being represented by formula (I-b-1), may also be prepared by cyclizing an intermediate of formula (XIII), which in situ may be formed by reacting an intermediate of formula (XIV) with a methanamine of formula (XV).

The thus obtained compounds of formula (I-b-1) may further be O-alkylated with a reagent $W-R^{1-b-1}$ thus preparing compounds of formula (I) wherein —A— is a bivalent radical of formula (a) and $R^1$ is $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy, said compounds being represented by the formula (I-b-2) and said radicals by $R^{1-b-1}$-o-.

In (XVI) W has the previously defined meanings and $R^{1-b-1}$ is $C_{1-10}$alkyl; $C_{1-6}$alkyl substituted with $Ar^1$ or $C_{3-7}$cycloalkyl; $C_{3-6}$alkenyl optionally substituted with $Ar^2$; $C_{3-6}$alkynyl optionally substituted with $Ar^2$; or $Ar^1$ and $W^1$ in (XIV) is an appropriate leaving group such as, for example, halo, preferably fluoro, chloro or bromo, a sulfonyloxy group, e.g., methylsulfonyloxy or 4-methylbenzenesulfonyloxy, or a $C_{1-6}$alkyloxy or $C_{1-6}$alkylthio group.

Said cyclizing reaction may be carried out in a suitable reaction-inert solvent such as, for example an alcohol, e.g., methanol, ethanol, 2-propanol and the like, and, if desired, in the presence of an appropriate base, such as, for example, an alkali or an earth alkaline metal carbonate, hydrogen carbonate, hydroxide or alkoxide.

Said O-alkylation is conveniently conducted in a suitable reaction-inert solvent or a mixture of such solvents. Suitable reaction-inert solvents are, for example, an aromatic hydrocarbon, e.g., benzene, methylbenzene, dimethylbenzene, and the like; a lower alkanol, e.g., methanol, ethanol, 1-butanol and the like; a polar aprotic solvent, e.g., N,N-dimethylformamide, N,N-dimethylacetamide, hexamethylphosphoric triamide, dimethyl sulfoxide; and the like. Preferably in the presence of an appropriate base such as, for example, an alkali metal hydride, alkoxide, hydroxide or carbonate. It may be advantageous previously to convert (I-b-1) into a metal salt thereof, preferably the sodium salt, in the usual manner, e.g., by the reaction of (I-b-1) with a metal base such as sodium hydroxide and the like, and thereafter to use said metal salt in the reaction with (XVI).

Compounds of formula (I), wherein —A— is a bivalent radical of formula (a), can also be prepared by reductively cyclizing an imidazole derivative of formula (XVII) in the presence of an appropriate reductant. Depending on the nature of the reductant and/or reaction conditions one may obtain compounds of formula (I-a-1) or compounds of formula (I-b-1), which may be converted to compounds of formula (I-a-2) or (I-b-2) respectively, as described hereinabove.

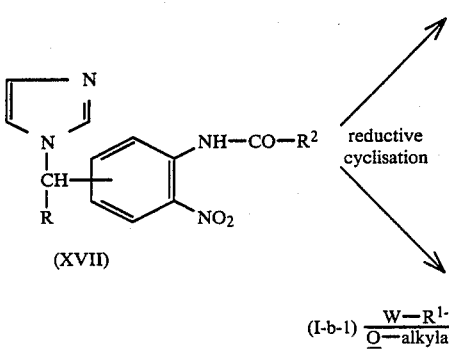

Appropriate reductants are for example, sodium borohydride, sodium dithionite or hydrogen gas, the latter being preferably used in the presence of a suitable catalyst such as, for example, palladium-on-charcoal, platinum-on-charcoal, Raney-nickel and the like.

The cyclizing reaction is most conveniently conoducted in a reaction-inert solvent such as, for example, an alkanol, e.g., methanol, ethanol, 2-propanol and the like. In the instance where compounds of formula (I-b-1) are desired, said reduction reaction is preferably conducted in the presence of an acid. In order to prevent the undesired further hydrogenation of certain functional groups in the reactants and the reaction products it may be advantageous to add an appropriate catalyst poison to the reaction mixture, e.g., thiophene and the like.

The compounds of formula (I), wherein —A— is a bivalent radical of formula (b) and $R^1$ is hydrogen, $C_{3-7}$cycloalkyl, $Ar^2$, $C_{1-10}$alkyl, or $C_{1-6}$alkyl substituted with $Ar^1$ or $C_{3-7}$cycloalkyl, said compounds being represented by formula (I-c) and said radical by $R^{1-c}$, may be formed by condensing a 1,2-benzenediamine of formula (XVIII) with a

group generating agent, (XIX), e.g., urea, thiourea, 1,1'-carbonylbis[1H-imidazole], alkylcarbonohalidate, carbonic dichloride, carbonothioic dichloride, trifluoromethyl carbonohalidate, carbon disulfide, cyanic acid, carbon dioxide, diethyl carbamic chloride and the like.

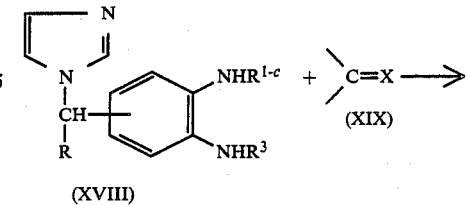

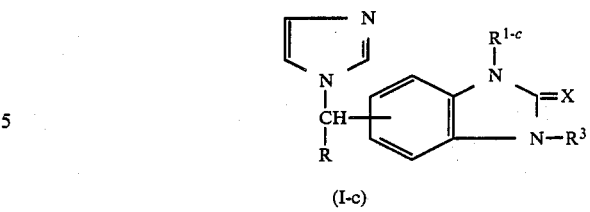

The reaction of (XVIII) with the $$\diagdown C=X \diagup$$

generating agent, (XIX), can conveniently be conducted in a suitable solvent such as, for example, an ether, e.g., 1,1'-oxybisethane, tetrahydrofuran; a halogenated hydrocarbon, e.g., dichloromethane, trichloromethane; a hydrocarbon, e.g., benzene, methylbenzene; an alcohol, e.g., methanol, ethanol; a ketone, e.g., 2-propanone, 4-methyl-2-pentanone; a polar aprotic solvent, e.g., N,N-dimethylformamide, N,N-dimethylacetamide, acetonitrile, or mixtures of such solvents, optionally in the presence of an appropriate base such as, for example, N,N-diethylethanamine, an alkali or earth alkaline metal carbonate or hydrogen carbonate. In order to enhance the reaction rate, it may be suitable to heat the reaction mixture. In some instances good results may obtained by stirring and heating the reactants in absence of any solvent.

The compounds of formula (I) can also be obtained by desulfurating an intermediate of formula (XX) in the usual manner, e.g., by treating the latter with Raney-nickel in the presence of an alcohol, e.g., ethanol or by treating the starting compounds with sodium nitrite in the presence of nitric acid in an aqueous medium.

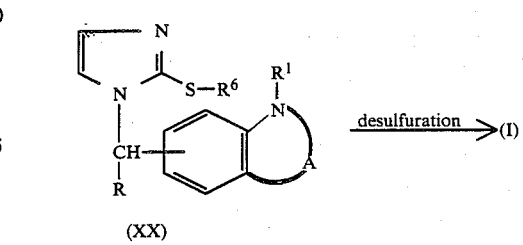

$R^6$ in (XX) is $C_{1-6}$alkyl.

The compounds of formula (I) may also be converted into each other following art-known functional gorup transformation procedures. A number of such procedures will be described hereinafter in more detail.

The compounds of formula (I-c) wherein $R^3$ is hydrogen may be converted into the corresponding compounds of formula (I-a) wherein $R^2$ is halo following art-known halogenating procedures, e.g., by reacting the former compounds with a suitable halogenating agent, e.g., hydrochloric acid, thionyl chloride, phosphoryl chloride, phosphorous trichloride, pentachlorophosphorane, thionyl bromide, phosphorous bromide and the like.

The halo substituent in the thus obtained compounds of formula (I-a) may further be converted in an imidazolyl substituent by stirring and heating the starting compounds with an 1H-imidazole, if desired, in the presence of a suitable solvent, such as, for example, N,N-dimethylformamide, N,N-dimethylacetamide and the like.

The compounds of formula (I) containing an ester group may be converted into the corresponding carboxylic acids following art-known saponification procedures, e.g., by treating the starting compounds with an aqueous alkaline or an aqueous acidic solution. Vice versa, the carboxylic acid group may be converted into the corresponding ester group following art-known esterification procedures. For example, the carboxylic acid may be converted into a reactive derivative which subsequently is reacted with the corresponding alkanol; or by reacting the carboxylic acid and the alkanol with a suitable reagent capable of forming esters, e.g., dicyclohexylcarbodiimide, 2-chloro-1-methylpyridinium iodide and the like.

The compounds of formula (I) wherein $R^2$ is an ester group may be converted into compounds of formula (I) wherein $R^2$ is hydrogen by stirring, and if desired, heating the starting compounds in the presence of an acid.

Compounds of formula (I) having a hydroxymethyl substituent may be oxidized under standard oxidation conditions by the action of an appropriate oxidans such as, for example, potassium permanganate, potassium dichromate and the like, to produce the corresponding carboxylic acid. Under similar reaction conditions compounds of formula (I) having a $Ar^2$—(CH—OH) substituent may be oxidized to the corresponding compounds having a $Ar^2$-carbonyl substituent.

The compounds of formula (I) may be converted to their therapeutically active non-toxic acid addition salt forms by treatment with appropriate acids, such as, for example, inorganic acids, such as hydrohalic acid, e.g., hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be convered by treatment with alkali into the free base form.

The compounds of formula (I) containing one or more acidic protons, may also be converted to their therapeutically active non-toxic metal or amine substitution salt forms by treatment with appropriate organic or inorganic bases. Appropriate inorganic bases may, for example, be ammonia or bases derived from alkali or earth alkaline metals, e.g., alkali metal or earth alkaline metal oxides or hydroxides such as lithium hydroxide, sodium hydroxide, potassium hydroxide, magnesium hydroxide, calcium hydroxide, calciumoxide and the like; alkalimetal or earth alkaline metal hydrides, e.g., sodium hydride, potassium hydride and the like; alkalimetal hydrogen carbonates or carbonates, e.g., sodium carbonate, potassium carbonate, sodium hydrogen carbonate, calcium carbonate and the like. Appropriate organic bases may, for example be primary, secondary and tertiary aliphatic and aromatic amines such as, for example, methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, N-methylmorpholine, trimethylamine, tripropylamine, quinuclidine, pyridine, quinoline, isoquinoline, diethanolamine and 1,4-diazabicyclo[2,2,2]octane; or quaternary ammonium bases e.g., tetramethylammonium hydroxide, trimethylbenzylammonium hydroxide, triethylbenzylammonium hydroxide, tetraethylammonium hydroxide, and trimethylethylammonium hydroxide.

Some intermediates and starting materials in the foregoing preparations are known compounds which may be prepared according to art-known methodologies of preparing said or similar compounds and others are new. A number of such preparation methods will be described hereinafter in more detail.

The starting materials of formula (II) wherein W represents a reactive ester group can be obtained by converting an intermediate of formula (IV) into a reactive ester following standard procedures as known in the art.

Halides are generally prepared by the reaction of (IV) with an appropriate halogenating agent such as, for example, thionyl chloride, sulfuryl chloride, pentachlorophoshorane, pentabromophoshorane, phosphoryl chloride and the like. When the reactive ester is a iodide it is preferably prepared from the corresponding chloride or bromide by the replacement of that halogen with iodine. Other reactive esters such as methanesulfonates and 4-methylbenzenesulfonates are obtained by the reaction of the alcohol with an appropriate sulfonyl halide such as, for example, methanesulfonyl chloride or 4-methylbenzenesulfonyl chloride respectively.

The intermediates of formula (IV), wherein —A— is a bivalent radical of formula (a) and $R^1$ is hydrogen, $C_{3-7}$cycloalkyl, $Ar^2$, $C_{1-10}$alkyl or $C_{1-6}$alkyl substituted with $Ar^1$ or $C_{3-7}$cycloalkyl, said intermediates being represented by formula (IV-a) can be prepared by reacting a ketone or aldehyde of formula (XXI) with a carboxylic acid of formula (VII) following procedures described for the preparation of (I-a) from (VI) and (VII) and subsequently reducing the aldehyde or ketone moiety with an appropriate reductant, e.g., sodium borohydride in a suitable solvent, e.g., methanol.

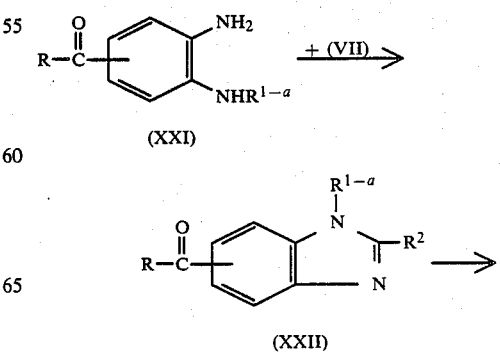

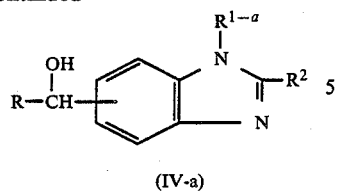

(IV-a)

The intermediates of formula (IV-a) wherein R is hydrogen, said intermediates being represented by formula (IV-a-1) may alternatively be prepared by reducing the formyl and nitro function in the intermediates of formula (XXIII) by catalytic hydrogenation in the prsence of an appropriate catalyst, e.g., Raney-nickel and subsequently reacting the thus obtained intermediate of formula (XXIV) with a carboxylic acid of formula (VII) following procedures described for the preparation of (I-a) from (VI) and (VII).

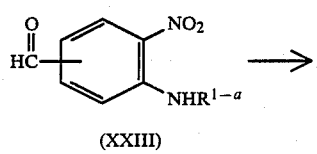

(XXIII)

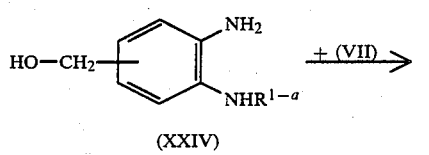

(XXIV)

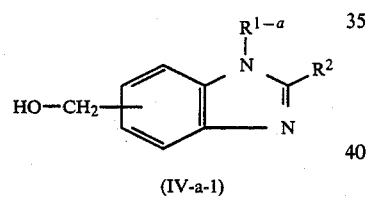

(IV-a-1)

In addition to the above the intermediateds of formula (IV-a-1) may also be prepared from an appropriately substituted benzoic acid of formula (XXV) according to the following reactions sequence.

An intermediate of formula (XXV) is reacted with an appropriate amine of formula (XXVI), wherein $R^{1-a}$ is a previously defined, in a similar manner as described hereinabove for the reaction of (XIV) with (XV). The thus obtained intermediate (XXVII) is then subjected to a nitro-to-amine reduction reaction, yielding an intermediate of formula (XXVIII). The latter is converted into a benzimidazole derivative of formula (XXIX) by cyclizing with an appropriate cyclizing agent as previously described for the preparation of compounds of formula (I-a). The carboxylic acid (XXIX) is then converted into the corresponding carbonyl chloride (XXX) in the usual manner, e.g., by the reaction with thionyl chloride, and the thus obtained (XXX) is then reacted with and appropriate $C_{1-6}$alkanol, (XXXI), to obtain a $C_{1-6}$alkyl ester of formula (XXXII). The latter is reduced to the corresponding alcohol, (IV-a-1) with an appropriate reducing agent, e.g., sodium dihydrobis-(2-methoxyethoxy) aluminate (Red-Al). Intermediates of formula (IV-a-1) may alternatively be prepared by reducing the carboxylic acid (XXIX) with borane-methyl sulfide complex in a suitable solvent, e.g., tetrahydrofuran.

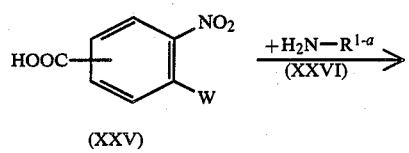

(XXV)

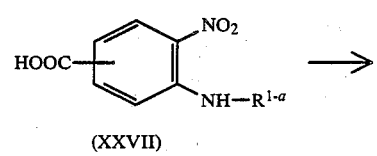

(XXVII)

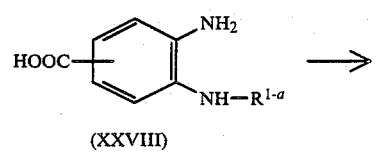

(XXVIII)

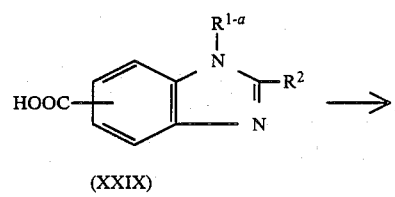

(XXIX)

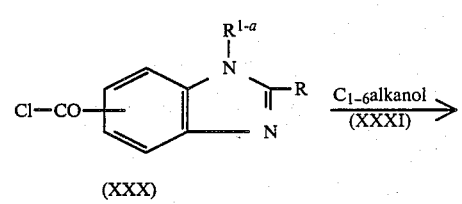

(XXX)

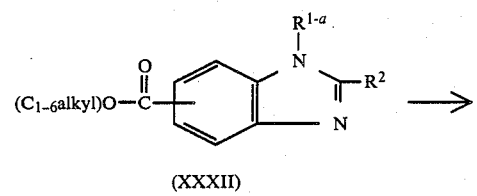

(XXXII)

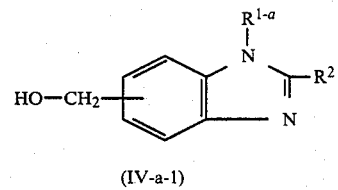

(IV-a-1)

In the above described reaction schemes $R^{1-a}$ is as previously defined.

The intermediates of formula (IV), wherein —A— is a bivalent radical of formula (a) and $R^1$ is hydroxy; $C_{1-10}$alkyloxy; $C_{1-6}$alkyloxy substituted with $Ar^1$ or $C_{3-7}$cyclalkyl; $C_{3-6}$alkenyloxy optionally substituted with $Ar^2$; $C_{3-6}$alkynyloxy optionally substituted with $Ar^2$ or $Ar^1$-oxy, said intermediates being represented by (IV-b) can, for example, be obtained by the following reaction sequence. A ketone or aldehyde of formula (XXXIII) may cyclised in the presence of an appropriate reductant following cyclizing procedures described hereinabove for the preparation of (I-b-1) from (XVII)

and, if desired, be O-alkylated following procedures described hereinabove for the preparation of (I-b-2). The desired alkanol of formula (IV-b) may then be obtained by reducing the aldehyde or ketone of formula (XXXV) with an appropriate reductant, e.g., sodium borohydride in a suitable solvent, e.g., methanol.

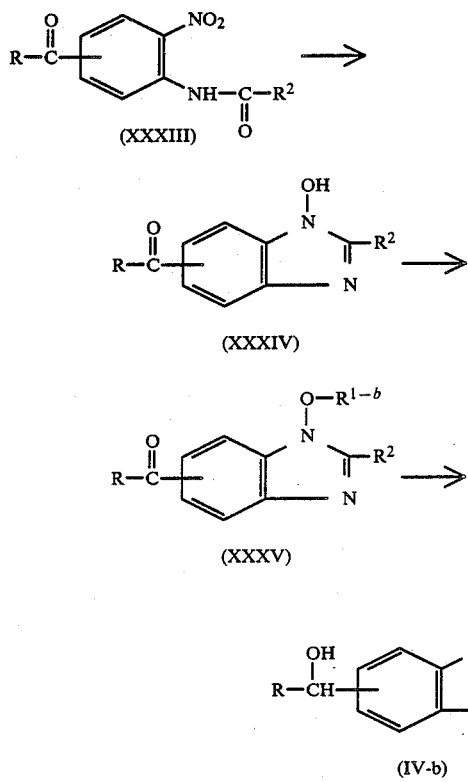

$R^{1-b}$ has the same meanings of the previously described $R^{1-b-1}$, and may also be hydrogen.

$R^{1-b}$ has the same meanings of the previously described $R^{1-b-1}$, and may also be hydrogen.

The intermediates of formula (IV) wherein R is other than hydrogen, said intermediates being represented by formula (IV-d) can also be obtained from the corresponding intermediates of formula (IV) wherein R is hydrogen, (IV-c), by oxidizing the hydroxymethyl function in (IV-c) to the corresponding formyl function with an appropriate oxidizing agent, e.g., manganese(IV) oxide, and reacting the thus obtained aldehyde (XXXVI) with a metal alkyl, e.g., methyllithium, butyllithium, metal aryl, e.g., phenyllithium, or with a complex metal alkyl in a suitable solvent, e.g., tetrahydrofuran.

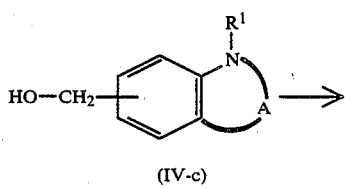

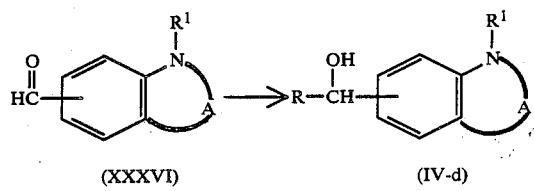

The benzenediamines of formula (VI), used as starting materials herein, can generally be prepared by the following sequence of reactions.

An intermediate of formula (XXXVII) is subsequently reducted with an appropriate reductant, such as, for example, sodium borohydride and converted into a reactive ester following standard procedures known in the art, yielding an intermediate of formula (XXXIX). The latter is reacted with 1H-imidazole (III) yielding and intermediate of formula (XIV). The thus obtained intermediate of formula (XIV) is reacted with an appropriate amine of formula (XXVI) and is subsequently subjected to a standard nitro-to-amine reduction reaction to yield the desired starting materials of formula (VI).

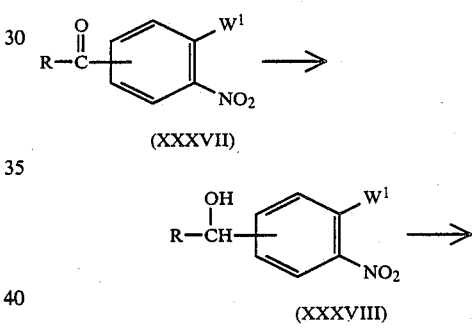

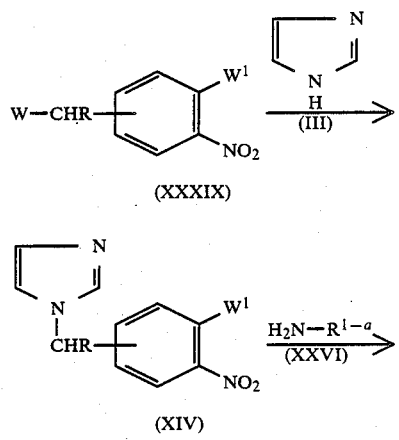

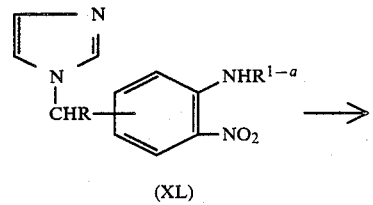

-continued

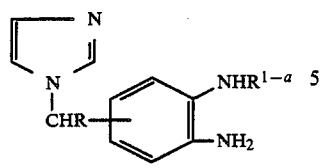

(VI)

In the above described reaction scheme $R^{1-a}$, W and $W^1$ are as previously defined.

Starting materials of formula (VI), wherein $R^{1-a}$ is hydrogen, said compoudns being represented by formula (VI-a), may alternatively be prepared according the following reaction sequence.

An 1H-imidazole (III) is reacted with an intermediate of formula (XLI) yielding an intermediate of formula (XLII). The latter is subsequently reduced, acylated, nitrated, deacylated and reduced to obtain a compound of formula (VI-a). Said nitro-to-amine reduction reaction is generally carried out by stirring the starting compound in a hydrogen containing medium in the presence of a suitable amount of an appropriate catalyst such as, for example, platinium-on-charcoal, palladium-on-charcoal, Raney-nickel and the like. The reduction may also be carried out by stirring the starting compound with sodium sulfide or sodium dithionite in a suitable solvent such as, for example water, methanol, ethanol and the like.

$C_{1-6}$alkylcarbonyl or arylcarbonyl groups may be introduced by reacting the amine with an appropriate carboxylic acid or a reactive derivative thereof following art-known amidation procedures.

The nitration reaction is conveniently conducted in a suitable solvent, such as, for example, a halogenated hydrocarbon, e.g., trichloromethane and the like in the presence of an appropriate acid, such as, for example, sulfuric acid, or a mixture of acetic acid and acetic acid anhydride.

The deacylation reaction is conveniently conducted by treating the intermediate compounds of formula (XVII) with an aqueous basic solution or an aqueous acidic solution.

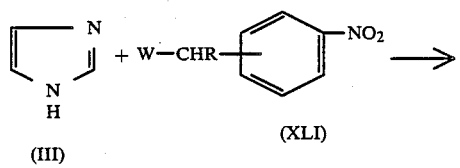

(III)  (XLI)

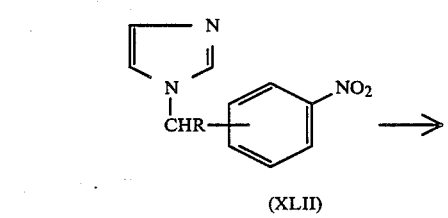

(XLII)

-continued

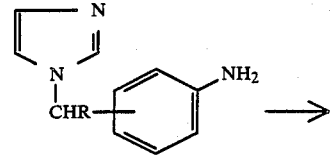

(XLIII)

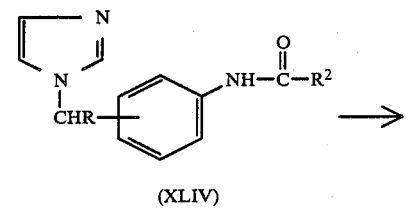

(XLIV)

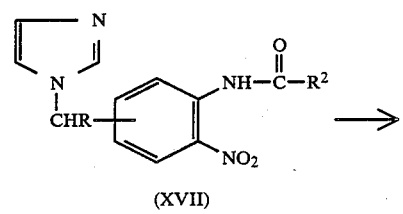

(XVII)

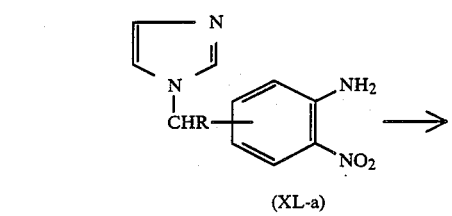

(XL-a)

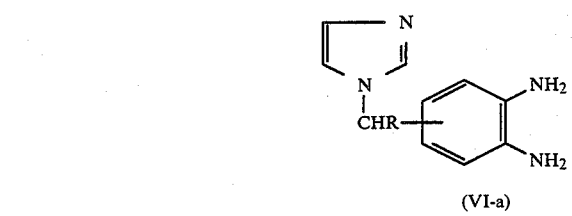

(VI-a)

Intermediates of formula (XL) which can easily be converted in compounds of formula (VI) can alternatively be obtained by reacting an intermediate of formula (XLV) with 1,1'-carbonylbis[1H-imidazole] following the same procedures as previously described herein for the preparation of (I) starting from (IV) and 1,1'-carbonylbis[1H-imidazole].

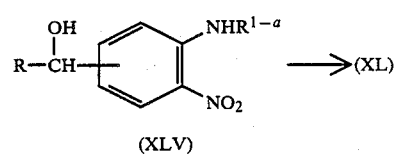

(XLV)

The intermediates of formula (XX) can be prepared by stirring and heating an appropriate isothiocyanate (XLVI), wherein $R^7$ is $C_{1-6}$alkyl or $Ar^2$-$C_{1-6}$alkyl, with an appropriately substituted amine (XLVII) in the presence of a suitable reaction-inert organic solvent such as for example, a halogenated hydrocarbon, e.g., dichloromethane; subsequently by converting the thus obtained thiourea (XLVIII) to the corresponding carbamimidothioate (XLIX) with a halogenide (L), wherein $R^6$ is $C_{1-6}$alkyl and Halo is preferably chloro, bromo or iodo, by stirring the reactants in the presence of an appropriate reaction-inert solvent, e.g., propanone; cyclizing the thus obtained carbamimidothioate (XLIX) by stirring and heating the latter in an aqueous acidic solvent, e.g., in aqueous sulfuric acid; and finally condensing the benzimidazole moiety following the cyclizing procedures described hereinabove.

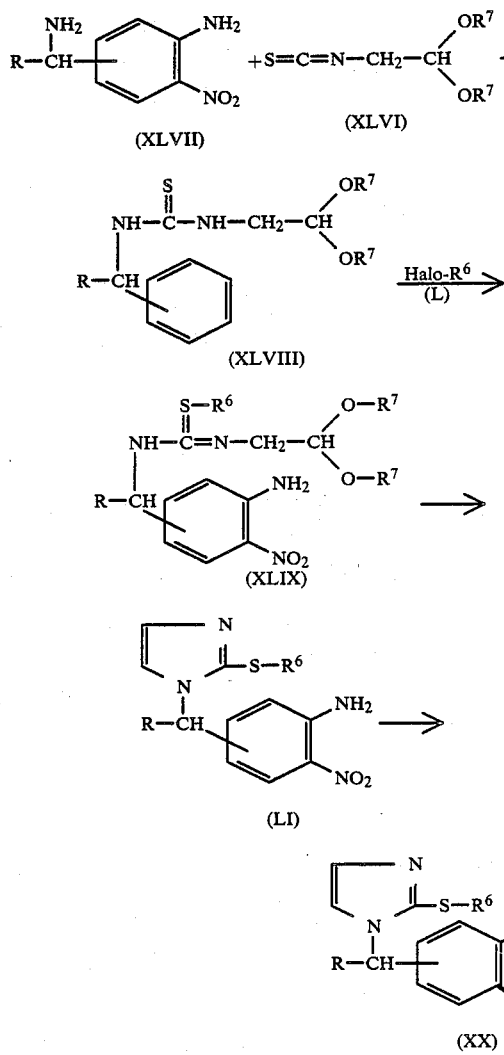

Starting materials and intermediates used in all of the preceding procedures for which no specific preparations are given herein, are generally known and/or may all be prepared following art-known methodologies described in the literature for the preparation of similar known compounds.

For example intermediates of formula (XXI) and (XXIII) may be prepared following similar procedures as described in U.S. Pat. No. 3,657,267 and J. Org. Chem. 44, pp. 4705 (1979) which are incorporated herein as reference.

The compounds of formula (I) and some of the intermediates in this invention may have an asymmetric carbon atom in their structure. This chiral center may be present in a R- and a S-configuration, this R- and S-notation being in correspondence with the rules described in J. Org. Chem., 35, 2849–2867 (1970).

Pure stereochemically isomeric forms of the compounds of this invention may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

Stereochemically isomeric forms of the compounds of formula (I) are naturally intended to be embraced within the scope of the invention.

The compounds of formula (I) and the pharmaceutically acceptable acid addition, metal or amine substitution salts and stereoisomeric forms thereof have very interesting pharmacological properties. They inhibit the androgen formation from $C_{21}$-steroids, such as pregnenolone and prostagens, in mammals and as such they can be used in the treatment of androgen dependent disorders. Further some of the compounds of formula (I) show the capability to increase the excretion of ureic acid, thus causing a decrease of the ureic acid levels in the plasma, and as such utility is indicated in various diseases which are related to increased levels of ureic acid, e.g., gout. In addition to the above, some of the compounds of formula (I) show an inhibitory action on the biosynthesis of thromboxane $A_2$.

The inhibition of androgen formation can be demonstrated in in vitro tests or in vivo tests, for example, by measuring testosterone biosynthesis in isolated testicular cell suspensions (in vitro) or in plasma of male rats or dogs (in vivo). In addition, the study of cytochrome P-450 isozymes may demonstrate the useful inhibitory properties of the compounds of formula (I), as it is generally known that cytochrome P-450 isozymes are involved in the biosynthesis of androgens from $C_{21}$-steroids (Journal of Biological Chemistry 256, 6134–6139 (1981)). The "Piglet Testes Microsomes" test and the "Testosterone in Vivo" test which are described hereinafter illustrate the androgen biosynthesis inhibitory properties of the compounds and are based on the above principles.

In view of their capability to inhibit the biosynthesis of androgenic hormones the compounds of the present invention can be used in the treatment of androgen dependent disorders such as, for example, prostatic cancer and hirsutism.

The beneficial effect of androgen inhibitors in these disorders, especially in the treatment of prostatic cancer, is described in, e.g., Journal of Urology 132, 61–63 (1984).

In view of the usefulness of the subject compounds in the treatment of androgen dependent disorders it is evident that the present invention provides a method of treating mammals suffering from said androgen dependent disorders. In particular there is provided a method of inhibiting androgen synthesis in mammals, particular a method of inhibiting the androgen formation from $C_{21}$-steroids in mammals. Said methods comprise the systemic administration to the latter of an amount, effective to treat androgen dependent disorders, of a compound of formula (I), a pharmaceutically acceptable acid-addition, metal or amine substitution salt or a stereoisomeric form thereof.

Those of skill in treating androgen dependent disorders could easily determine the effective amount from the test results presented hereinafter. In general it is contemplated that an effective amount would be from 0.05 mg/kg to 50 mg/kg body weight, and more preferably for 0.5 mg/kg to 10 mg/kg body weight.

Particularly in treating prostatic cancer the effective amount would be that amount which lowers the serum androgens to about castration levels.

In view of the above mentioned capability of reducing the ureic acid levels in plasma there is provided a method of treating mammals suffering from increased levels of ureic acid. Said method comprises the systemic administration to the latter of an amount, effective to treat increased levels of ureic acid, of those compounds of formula (I) which decrease the ureic acid levels, e.g., 5-[(1H-imidazol-1-yl)phenylmethyl]-2-methyl-1H-benzimidazole, a pharmaceutically acceptable acid-addition, metal or amine substitution salt or a stereoisomeric form thereof.

Doses effective in reducing the ureic acid levels in plasma would be from 0.01 mg/kg to 20 mg/kg body weight, and more preferably from 0.1 to 2 mg/kg body weight.

In view of their useful pharmacological properties, the subject compounds may be formulated into various pharmaceutical forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment.

The following examples are intended to illustrate and not to limit the scope of the invention. Unless otherwise stated all parts therein are by weight.

EXPERIMENTAL PART

A. Preparation of Intermediates

Example 1

(a-1) A solution of 40 parts of 4-chloro-3-nitrobenzaldehyde and 338 parts of 1-propanamine was stirred and refluxed for 1.50 hour. The reaction mixture was evaporqted, yielding 53.7 parts of 2-nitro-N-propyl-4-[(propylimino)methyl]benzenamine as a residue (int. 1).

(a-2) A mixture of 53.7 parts of 2-nitro-N-propyl-4-[(propylimino)methyl]benzenamine, 360 parts of concentrated hydrochloric acid and 300 parts of water was stirred and refluxed for 30 minutes. The reaction mixture was cooled and the product was extracted with trichloromethane. The extract was dried, filtered and evaporated. The residue was purified by column chromatography over silica gel using trichloromethane as eluent. The pure fractions were collected and the eluent was evaporated, yielding 20.4 parts of 3-nitro-4-(propylamino)benzaldehyde; mp. 73.6° C. (int. 2)

(a-3) A mixture of 10.4 parts of 3-nitro-4-(propylamino)benzaldehyde and 200 parts of methanol was hydrogenated in the Parr-apparatus with 3 parts of Raney-nickel catalyst. After the calculated amount of hydrogen was taken up, the catalyst was filtered off and the filtrate was acidified with 3 parts of acetic acid. The solvent was evaporated, yielding 12 parts (100%) of 3-amino-4-(propylamino)benzenemethanol acetate (1:1) as a residue (int. 3).

(a-4) A mixture of 8 parts of 3-amino-4-(propylamino)benzenemethanol, 14.05 parts of ethyl 3-pyridinecarboximidate dihydrochloride, 9.8 parts of sodium acetate and 96 parts of ethanol was stirred for 16 hours at room temperature. The reaction mixture was evaporated. The residue was dissolved in water and treated with ammonia. The precipitated product was filtered off, washed with water and dissolved in dichloromethane. The organic layer was dried, filtered and evaporated. The residue was washed with 2,2'-oxybispropane, yielding 9.9 parts (84.1%) of 1-propyl-2-(3-pyridinyl)-1H-benzimidazole-5-methanol as a residue (interm. 4).

In a similar manner there were also prepared:

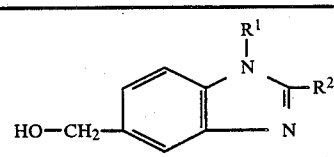

| Int. No. | $R^1$ | $R^2$ | salt base | mp. (°C.) |
|---|---|---|---|---|
| 5 | H | $CH_3$ | HCl | 200 |
| 6 | H | $C_6H_5$ | HCl | 220 |
| 7 | H | $CH_3-CH_2-CH_2$ | base | — |
| 8 | H | $CH_3-CH_2$ | base | — |
| 9 | $CH_3-CH_2-CH_2$ | H | base | 94.8 |
| 10 | $CH_3$ | H | base | 152.3 |
| 11 | $CH_3$ | $C_6H_5$ | base | 148 |
| 12 | $CH_3$ | $CH_3-CH_2$ | HCl | 234.8 |
| 13 | $CH_3-CH_2-CH_2$ | $CH_3-CH_2$ | HCl | — |

-continued

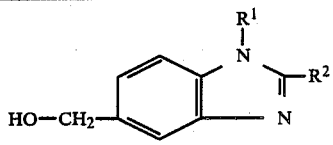

| Int. No. | R$^1$ | R$^2$ | salt base | mp. (°C.) |
|---|---|---|---|---|
| 14 | CH$_3$ | CF$_3$ | base | — | and 1,3-dihydro-5-(hydroxymethyl-2H—benzimidazole-2-one; mp. 238.2° C. (15).

(b-1) To a stirred solution of 4.01 parts of 1-propyl-2-(3-pyridinyl)-1H-benzimidazole-5-methanol in 65 parts of dichloromethane and 3 parts of N,N-diethylethanamine were added 2.23 parts of methanesulfonyl chloride. The whole was stirred for 45 minutes at room temperature. The mixture was poured into crushed ice and the dichloromethane layer was separated, dried, filtered and evaporated. The residue was dissolved in methylbenzene. The precipitate was filtered off and the filtrate was evaporated, yielding 2.3 parts (66%) of 5-(chloromethyl)-1-propyl-2-(3-pyridinyl)-1H-benzimidazole as a residue (int. 16).

In a similar manner there were also prepared:

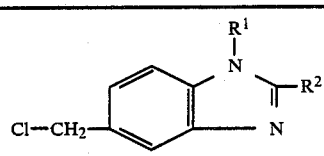

| Int. No. | R$^1$ | R$^2$ | salt base | mp. (°C.) |
|---|---|---|---|---|
| 17 | H | CH$_3$ | HCl | 205 |
| 18 | H | C$_6$H$_5$ | HCl | 228 |
| 19 | H | CH$_3$—CH$_2$—CH$_2$ | HCl | — |
| 20 | H | CH$_3$—CH$_2$ | HCl | — |
| 21 | CH$_3$ | CH$_3$ | HCl | 204 |
| 22 | CH$_3$—CH$_2$—CH$_2$ | H | HCl | 165.6 |
| 23 | CH$_3$ | H | HCl.½H$_2$O | 169.3 |
| 24 | CH$_3$ | C$_6$H$_5$ | HCl | 210.7 |
| 25 | CH$_3$ | CH$_3$—CH$_2$ | HCl | — |
| 26 | CH$_3$—CH$_2$—CH$_2$ | CH$_3$—CH$_2$ | HCl | — |
| 27 | CH$_3$ | CF$_3$ | HCl | — | and 5-(chloromethyl)-1,3-dihydro-2H—benzimidazol-2-one (int. 28).

Example 2

(a-1) To a stirred solution of 1.4 parts of ethyl glycine hydrochloride in 10 parts of water was added a solution of 1.7 parts of 4-fluoro-3-nitrobenzaldehyde in 8 parts of ethanol. Then there were added 1.76 parts of sodium hydrogen carbonate and stirring at room temperature was continued for 48 hours. The precipitated product was filtered off, washed successively with water, ethanol and 2,2'-oxybispropane, and dried, yielding 2 parts (79%) of ethyl N-(4-formyl-2-nitrophenyl)-glycine; mp. 90° C. (int. 29).

(a-2) To a stirred solution of 47.8 parts of ethyl N-(4-formyl-2-nitrophenyl)glycine in 280 parts of ethanol were added in small portions 3.8 parts of sodium tetrahydroborate. The whole was stirred for 30 minutes at room temperature. The reaction mixture was decomposed by a solution of 12 parts of acetic acid in 50 parts of water. The mixture was concentrated. The product was extracted with dichloromethane. The extract was dried, filtered and evaporated. The residue was crystallized from 2-propanol. The product was filtered off and dried, yielding 34.1 parts (70.6%) of ethyl N-[4-(hydroxymethyl)-2-nitrophenyl]glycine (int. 30).

(a-3) A mixture of 2.6 parts of ethyl N-[4-(hydroxymethyl)-2-nitrophenyl]glycine, 8.3 parts of potassium carbonate and 40 parts of ethanol was stirred and refluxed for 2 hours. After cooling, a solution of 7.2 parts of acetic acid in 8 parts of ethanol was added and stirring was continued for 1 hour. The reaction mixture was evaporated. The residue was purified by column chromatography over silica gel using a mixture of trichloromethane and methanol (90:10 by volume) as eluent. The pure fractions were collected and the eluent was evaporated. The residue was converted into the hydrochloride salt in 2-propanol. The salt was filtered off and dried, yielding 1.1 parts (40%) of ethyl 1-hydroxy-6-(hydroxymethyl)-1H-benzimidazole-2-carboxylate monohydrochloride; mp. 178.0° C. (int. 31).

(a-4) To a stirred soluiton of 0.92 parts of sodium in 32 parts of ethanol were added 5.46 parts of ethyl 1-hydroxy-6-(hydroxymethyl)-1H-benzimidazole-2-carboxylate monohydrochloride. The whole was stirred for 10 minutes and concentrated. 18 Parts of methylbenzene were added and the mixture was evaporated. 13.5 Parts of N,N-dimethylformamide and a solution of 2.84 parts of iodomethane in 4.5 parts of N,N-dimethylformamide were added. After stirring for 30 minutes, the reaction mixture was evaporated. The residue was purified by column chromatography over silica gel using a mixture of trichloromethane and acetonitrile (80:20 by volume) as eluent. The pure fractions were collected and the eluent was evaporated. The residue was crystallized from a mixture of 2-propanol and 2,2'-oxybispropane (1:4 by volume). The product was filtered off and dried, yielding 2.5 parts (50%) of ethyl 6-(hydroxymethyl)-1-methoxy-1H-benzimidazole-2-carboxylate; mp. 110.1° C. (int. 32).

(a-5) A mixture of 4.2 parts of ethyl 6-(hydroxymethyl)-1-methoxy-1H-benzimidazole-2-carboxylate and 60 parts of concentrated hydrochloric acid was stirred for 1 hour at reflux temperature. The reaction mixture was concentrated and the residue was crystallized from 2-propanol. The product was filtered off and dried, yielding 3.1 parts (79.2%) of 6-(chloromethyl)-1-methoxy-1H-benzimidazole monohydrochloride; mp. 158° C. (int. 33).

Example 3

(a-1) A mixture of 20 parts of (3,4-diaminophenyl) (3-fluorophenyl) methanone, 27 parts of ethyl ethanimidate hydrochloride and 80 parts of methanol was stirred for 17 hours at reflux temperature. The reaction mixture was filtered and the filtrate was evaporated. The residue was taken up in a potassium carbonate solution 10% and the product was extracted with ethyl acetate. The extract was dried, filtered and evaporated. The residue was purified by column chromatography over silica gel using a mixture of dichloromethane and methanol (95:5 by volume) as eluent. The pure fractions were collected and the eluent was evaporated, yielding 15.6 parts (70.5%) of 3-fluorophenyl) (2-methyl-1H-benzimidazol-5-yl)methanone as a residue (int. 34).

(a-2) To a stirred solution of 14 parts of (3-fluorophenyl) (2-methyl-1H-benzimidazol-5-yl)methanone in 80 parts of methanol were added portionwise 5 parts of sodium tetrahydroborate at room temperature. Upon complete addition, stirring was continued for 1 hour at room temperature. The reaction mixture was poured into water and the product was extracted with ethyl acetate. The extract was dried, filtered and evaporated. The residue was converted into the hydrochloride salt in 80 parts of methanol and ethanol. The mixture was concentrated to dry, yielding 15.1 parts (93.7%) of α-(3-fluorophenyl)-2-methyl-1H-benzimidazole-5-methanol monohydrochloride as a residue (int. 35).

In a similar manner there were also prepared:
2-methyl-α-phenyl-1H-benzimidazole-5-methanol hydrochloride; mp. >300° C. (dec.) (int. 36);
1-methyl-α-phenyl-1H-benzimidazole-5-methanol; mp. 170.7° C. (int. 37);
1,2-dimethyl-α-phenyl-1H-benzimidazole-6-methanol; mp. 206.6° C. (38);
1-methyl-2,α-diphenyl-1H-benzimidazole-6-methanol as a residue (39);
2-phenyl-α-(2-thienyl)-1H-benzimidazole-5-methanol; mp. 243° C. (40);
2-(4-thiazolyl)-α-(2-thienyl)-1H-benzimidazole-5-methanol (int. 41);
α-(5-bromo-2-furanyl)-1H-benzimidazole-5-methanol as a residue (42);
α-(2-furanyl)-1H-benzimidazole-5-methanol as a residue (int. 43); and
α-(3-fluorophenyl)-1H-benzimidazole-5-methanol as a residue (int. 44).

(b-1) A mixture of 13 parts of α-(3-fluorophenyl)-2-methyl-1H-benzimidazole-5-methanol monohydrochloride and 81 parts of thionyl chloride was stirred overnight at room temperature. The reaction mixture was concentrated to dry, yielding 12 parts (86.8%) of 5-[chloro(3-fluorophenyl)methyl]-2-methyl-1H-benzimidazole monohydrochloride as a residue (int. 45).

In a similar manner there were also prepared:
2-methyl-α-phenyl-1H-benzimidazole-5-methanol methanesulfonate(ester) as a residue (int. 46); and
5-[chloro(3-fluorophenyl)methyl]-1H-benzimidazole as a residue (int. 47).

Example 4

(a-1) To a stirred solution of 16 parts of phenyl (3-amino-4-nitrophenyl) methanone in 195 parts of dichloromethane were added 7.8 parts of acetyl chloride. After stirring for 17 hours at room temperature, the reaction mixture was evaporated. The residue was crystallized from a mixture of ethyl acetate and 2,2'-oxybispropane. The product was filtered off and dried, yielding 15 parts (81%) of N-(5-benzoyl-2-nitrophenyl)acetamide; mp. 97.8° C. (int. 48).

(a-2) A mixture of 5.6 parts of N-(5-benzoyl-2-nitrophenyl)acetamide, 2 parts of a solution of thiophene in methanol 4%, 200 parts of methanol and 7 parts of 2-propanol, saturated with hydrogen chloride was hydrogenated at normal pressure and at room temperature with 1 part of platinum-on-charcoal catalyst 5%. After the calculated amount of hydrogen was taken up, the catalyst was filtered off and the filtrate was evaporated. The residue was washed with 2-propanone and dried, yielding 4.2 parts (73%) of (1-hydroxy-2-methyl-1H-benzimidazol-5-yl) phenylmethanone monohydrochloride as a residue (int. 49).

(a-3) 11.55 Parts of (1-hydroxy-2-methyl-1H-benzimidazol-5-yl) phenyl methanone monohydrochloride were added to a stirred solution of 1.84 parts of sodium in 80 parts of methanol. After stirring for 15 minutes at room temperature, the solvent was evaporated and the residue was taken up in methylbenzene. After evaporation, the residue was dissolved in 54 parts of N,N-dimethylformamide and 6.24 parts of iodomethane were added. The reaction mixture was stirred for 2 hours at room temperature. The N,N-dimethylformamide layer was evaporated in vacuo. The residue was taken up in water and the product was extracted with methylbenzene. The extract was dried, filtered and evaporated. The residue was washed with 2,2'-oxybispropane, yielding 6.4 parts (60.0%) of (1-methoxy-2-methyl-1H-benzimidazol-5-yl) phenylmethanone; mp. 67.7° C. (int. 50).

(a-4) To a stirred solution of 3.4 parts of (1-methoxy-2-methyl-1H-benzimidazol-5-yl) phenylmethanone in 64 parts of methanol were added 0.6 parts of sodium tetrahydroborate. After stirring for 30 minutes at room temperature, the methanol layer was evaporated. Water was added to the residue and the product was extracted with dichloromethane. The extract was dried, filtered and evaporated. The residue was crystallized from 45 parts of ethyl acetate. The product was filtered off and dried, yielding 2.8 parts (80%) of 1-methoxy-2-methyl-α-phenyl-1H-benzimidazole-5-methanol (int. 51).

In a similar manner there were also prepared:
1-methoxy-α,2-diphenyl-1H-benzimidazole-6-methanol (int. 52);
1-methoxy-α,2-diphenyl-1H-benzimidazole-5-methanol; mp. 142.4° C. (53);
1-methoxy-α-phenyl-1H-benzimidazole-6-methanol (int. 54);
1-methoxy-α,2-dimethyl-1H-benzimidazole-6-methanol (int. 55); and
1-methoxy-2-methyl-α-phenyl-1H-benzimidazole-6-methanol (int. 56).

Example 5

(a-1) A mixture of 104 parts of ethyl benzenecarboximidate hydrochloride, 97.1 parts of 3-amino-4-(propylamino)benzoic acid and 1200 parts of acetic acid was stirred for 60 minutes at room temperature and the for 20 hours at reflux. The reaction mixture was evaporated and water was added to the residue. The precipitated product was filtered off, washed with water and with acetonitrile and crystallized from acetic acid, yielding 58.5 parts of 2-phenyl-1propyl-1H-benzimidazole-5-carboxylic acid; mp. 223.4° C. (int. 57)

(a-2) To a stirred solution of 112.13 parts of 2-phenyl-1-propyl-1H-benzimidazole-5-carboxylic acid in 525 parts of trichloromethane were added 142 parts of thionyl chloride. Stirring was continued for 30 minutes at reflux temperature. The reaction mixture was evaporated, yielding 134 parts (100%) of 2-phenyl-1-propyl-1H-benzimidazole-5-carbonyl chloride monohydrochloride as a residue (int. 58).

(a-3) To a stirred solution of 134 parts of 2-phenyl-1-propyl-1H-benzimidazole-5-carbonyl chloride monohydrochloride in 300 parts of trichloromethane were added 240 parts of methanol and stirring was continued for 20 minutes at reflux temperature. The reaction mixture was evaporated. The residue was washed with 4-methyl-2-pentanone and dissolved in water. The free base was liberated in the conventional manner with ammonium hydroxide and extracted with methylbenzene. The extract was dried, filtered and evaporated. The residue was crystallized from 175 parts of 2.2'-oxybispropane. The product was filtered off and dried, yielding 91 parts (77.3%) of methyl 2-phenyl-1-propyl-1H-benzimidazole-5-carboxylate; mp. 79.8° C. (int. 59).

(a-4) To a stirred and cooled (ice-bath) solution of 103.9 parts of sodium dihydro-bis(2-methoxyethoxy)aluminate in 45 parts of methylbenzene was added dropwise a solution of 88.5 parts of methyl 2-phenyl-1-propyl-1H-benzimidazole-5-carboxylate in 270 parts of methylbenzene. Upon completion, stirring was continued for 1 hour at room temperature. The reaction mixture was decomposed by the addition of a mixture of 200 parts of a sodium hydroxide solution 7.5 N and 200 parts of water. The methylbenzene-phase was separated, dried, filtered and evaporated. The residue was washed with 210 parts of 2,2'-oxybispropane. The product was filtered off and dried, yielding 73 parts (91%) of 2-phenyl-1-propyl-1H-benzimidazole-5-methanol; mp. 112.9° C. (int. 60).

(a-5) A solution of 70.5 parts of 2-phenyl-1-propyl-1H-benzimidazole-5-methanol in 300 parts of trichloromethane was saturated with gaseous hydrogen chloride. Then there are added dropwise 55.9 parts of thionyl chloride (exothermic reaction). Upon completion, stirring was continued for 30 minutes at reflux temperature. The reaction mixture was evaporated, the residue was taken up in 90 parts of methylbenzene and the latter was evaporated again. The residue was crystallized from 320 parts of 4-methyl-2-pentanone, yielding 80 parts (96%) of 5-(chloromethyl)-2-phenyl-1-propyl-1H-benzimidazole monohydrochloride; mp. 138.5° C. (int. 61).

In a similar manner there were also prepared:
4-(chloromethyl)-1H-benzimidazole monohydrochloride as a residue (62);
7-(chloromethyl)-2-(3-pyridinyl)-1H-benzimidazole dihydrochloride as a residue (int. 63); and
7-(chloromethyl)-2-phenyl-1H-benzimidazole (int. 64).

Example 6

(a-1) A mixture of 17 parts of ethyl 2,3-diaminobenzoate, 14 parts of ethyl ethanimidate hydrochloride and 240 parts of ethanol was stirred for 19 hours at reflux temperature. After evaporation, the residue was taken up in a potassium carbonate solution 10% and the product was extracted with trichloromethane. The extract was dried, filtered and evaporated, yielding 19 parts (98.6%) of ehtyl 2-methyl-1H-benzimidazole-4-carboxylate as a residue (int. 65).

(a-2) A cooled (0° C.) solution of 10 parts of ethyl 2-methyl-1H-benzimidazole-4-carboxylate in 45 parts of tetrahydrofuran was added dropwise to a suspension of 4 parts of lithium tetrahydroaluminate in 45 parts of tetrahydrofuran. Upon complete addition, the temperature was allowed to reach room temperature. After the addition of ethyl acetate and water, the reaction mixture was filtered over diatomaceous earth. The filtrate was evaporated, yielding 6.3 parts (79.4%) of 2-methyl-1H-benzimidazole-4-methanol as a residue (int. 66).

(a-3) A mixture of 10 parts of 2-methyl-1H-benzimidazole-4-methanol, 10 parts of manganese(IV) oxide and 180 parts of ethyl acetate was stirred for 19 hours at room temperature. The reaction mixture was filtered over diatomaceous earth and washed with a mixture of ethyl acetate and methanol (80:20 by volume). The filtrate was evaporated and the residue was crystallized from 2-butanone. The product was filtered off and dried, yielding 3.5 parts (35.2%) of 2-methyl-1H-benzimidazole-4-carboxaldehyde (int. 67).

(a-4) To a stirred solution of 3 parts of 2-methyl-1H-benzimidazole-4-carboxaldehyde in 45 parts of dry tetrahydrofuran were added 15.3 parts of lithiumphenyl at 20° C. The reaction mixture was stirred for 30 minutes at room temperature. The mixture was poured into water. The precipitated product was filtered off and dried, yielding 4 parts (89.7%) of 2-methyl-α-phenyl-1H-benzimidazole-4-methanol (int. 68).

Example 7

(a-1) To a stirred solution of 41 parts of 4-fluoro-3-nitrobenzenemethanol and 39 parts of N,N-diethylethanamine in 325 parts of dichloromethane was added dropwise a solution of 30.3 parts of methanesulfonyl chloride in 65 parts of dichloromethane at a temperature between 0° and −5° C. The whole was stirred for 1 hour at 0° C. 100 Parts of ice water were added. The dichloromethane layer was decanted, dried, filtered and evaporated. The residue was purified by column chromatography over silica gel using trichloromethane as eluent. The pure fractions were collected and the eluent was evaporated. 35 Parts of 1,1'-oxybisethane were added to the residue. The produce was filtered off and dried, yielding 35.9 parts (60%) of 4-fluoro-3-nitrobenzenemethanol methanesulfonate(ester) (int. 69).

(a-2) To a stirred solution of 10.5 parts of 1H-imidazole in 80 parts of acetonitrile were added 17.5 parts of 4-fluoro-3-nitrobenzenemethanol methanesulfonate(ester) at once. The mixture was stirred and refluxed for 15 minutes. After cooling, the precipitate was filtered off and the filtrate was evaporated. The residue was purified by column chromatography over silica gel using a mixture of trichloromethane and methanol (95:5 by volume) as eluent. The pure fractions were collected and the eluent was evaporated. The solid residue was washed with 2,2'-oxybispropane and dried, yielding 6.5 parts (42%) of 1-[(4-fluoro-3-nitrophenyl)methyl]-1H-imidazole (int. 70).

(a-3) A mixture of 4.4 parts of 1-[(4-fluoro-3-nitrophenyl)methyl]-1H-imidazole, 4.33 parts of 3-pyridinemethanamine and 80 parts of absolute ethanol was stirred for 4 hours at reflux temperature. The reaction mixture was evaporated. 50 Parts of water were added to the residue. The product was extracted twice with 130 parts of trichloromethane. The combined trichloromethane layers were dried, filtered and evaporated. The residue was crystallized from 48 parts of 2-propanol. The product was filtered off and dried, yielding 5.1 parts (82%) of N-[4-(1H-imidazol-1-ylmethyl)-2-nitrophenyl]-3-pyridinemethanamine; mp. 171.0° C. (int. 71).

In a similar manner there were also prepared:
N-[4-(1H-imidazol-1-ylmethyl)-2-nitrophenyl]benzenemethanamine; mp. 110.2° C. (int. 72);
4-(1H-imidazol-1-ylmethyl)-N-methyl-2-nitrobenzenamine; mp. 160.3° C. (73);
4-fluoro-N-[4-(1H-imidazol-1-ylmethyl)-2-nitrophenyl]benzenemethanamine; mp. 116.7° C. (int. 74);
N-[5-(1H-imidazol-1-ylmethyl)-2-nitrophenyl]benzenemethanamine; mp. 81.8° C. (int. 75);
5-(1H-imidazol-1-ylmethyl)-N-methyl-2-nitrobenzenamine; mp. 124.2° C. (76);
N-[5-(1H-imidazol-1-ylmethyl)-2-nitrophenyl]benzeneethanamine; mp. 128.5° C. (int. 77);
N-(cyclohexylmethyl)-5-(1H-imidazol-1-ylmethyl)-2-nitrobenzenamine; mp. 58.2° C. (int. 78); and
N-[5-(1H-imidazol-1-ylmethyl)-2-nitrophenyl]cylcoheptanamine; mp. 129.6° C. (int. 79).

(b-1) A mixture of 6.2 parts of N-[4-(1H-imidazol-1-ylmethyl)-2-nitrophenyl]-3-pyridinemethanamine, 1 part of a solution of thiophene in methanol 4% and 200 parts of methanol was hydrogenated at normal pressure and at 50° C. with 2 parts of platinum-on-charcoal catalyst 5%. After the calculated amount of hydrogen was taken up, the catalyst was filtered off and the filtrate was evaporated, yielding 5.6 parts (100%) of 4-(1H-imidazol-1-ylmethyl)-N$^1$-(3-pyridinylmethyl)-1,2-benzenediamine as a residue (int. 80).

In a similar manner there were also prepared:
4-(1H-imidazol-1-ylmethyl)-N$^1$-methyl-1,2-benzenediamine (int. 81);
4-(1H-imidazol-1-ylmethyl)-N$^2$-(phenylmethyl)-1,2-benzenediamine (82);
4-(1H-imidazol-1-ylmethyl)-N$^2$-methyl-1,2-benzenediamine (int. 83);
4-(1H-imidazol-1-ylmethyl)-N$^2$-(2-phenylethyl)-1,2-benzenediamine (84);
N$^2$-(cyclohexylmethyl)-4-(1H-imidazol-1-ylmethyl)-1,2-benzenediamine (int. 85); and
N$^2$-cycloheptyl-4-(1H-imidazol-1-ylmethyl)-1,2-benzenediamine (86).

Example 8

(a-1) To a stirred and cooled solution of 50 parts of 1-(4-chloro-3-nitrophenyl)ethanone in 240 parts of methanol was added a solution of 40 parts of methanamine in 160 parts of methanol. The reaction mixture was stirred for 12 hours at 60° C. The reaction mixture was evaporated to dry, yielding 50 parts (100%) of 1-[4-(methylamino)-3-nitrophenyl]ethanone as a residue (int. 87).

(a-2) To a stirred mixture of 19.4 parts of 1-[4-(methylamino)-3-nitrophenyl]ethanone and 160 parts of methanol were added dropwise 4 parts of sodium tetrahydroborate. Upon complete addition, stirring was continued for 1 hour at room temperature. The reaction mixture was poured into 1000 parts of water and the product was extracted three times with 120 parts of trichloromethane. The combined extracts were dried, filtered and evaporated. The residue was purified by column chromatography over silica gel using a mixture of trichloromethane and methanol (98:2 by volume) as eluent. The pure fractions were collected and the eluent was evaporated, yielding 17 parts (89%) of α-methyl-4-(methylamino)-3-nitrobenzenemethanol as a residue (int. 88).

(a-3) A mixture of 17 parts of α-methyl-4-(methylamino)-3-nitrobenzenemethanol, 28 parts of 1,1'-carbonylbis[1H-imidazole] and 180 parts of tetrahydrofuran was stirred for 24 hours at room temperature. The reaction mixture was poured into a mixture of ice water and a potassium carbonate solution 30% and the product was extracted three times with 150 parts of trichloromethane. The combined extracts were dried, filtered and evaporated, yielding 21 parts (99.1%) of 4-[1-(1H-imidazol-1-yl)ethyl]-N-methyl-2-nitrobenzenamine as a residue (int. 89).

In a similar manner there were also prepared:
4-fluoro-N-[4-[(1H-imidazol-1-yl)phenylmethyl]-2-nitrophenyl]benzenemethanamine; mp. 67.7° C. (int. 90);
4-[(1H-imidazol-1-yl)phenylmethyl]-N-methyl-2-nitrobenzenamine; mp. 159.5° C. (int. 91);
N-[4-[1-(1H-imidazol-1-yl)ethyl]-2-nitrophenyl]benzenemethanamine (92);
4-fluoro-N-[4-[1-(1H-imidazol-1-yl)ethyl]-2-nitrophenyl]benzenemethanamine as a residue (int. 93);
4-fluoro-N-[4-[1-(1H-imidazol-1-yl)-2-methylpropyl]-2-nitrophenyl]benzene methanamine as a residue (int. 94);
N-[4-[1-(1H-imidazol-1yl)-2-methylpropyl]-2-nitrophenyl]benzenemethanamine as a residue (int. 95); and
4-[1-(1H-imidazol-1-yl)-2-methylpropyl]-N-methyl-2-nitrobenzenamine (96).

(b-1) A mixture of 21 parts of 4-[1-(1H-imidazol-1-yl)ethyl]-N-methyl-2-nitrobenzenamine and 160 parts of ethanol was hydrogenated at room temperature in a Parr apparatus at 0.5 10$^5$Pa with 20 parts of Raney-nickel catalyst. After the calculated amount of hydrogen was taken up, nitrogen was bubbled through the mixture and the catalyst was filtered off over diatomaceous earth. The filtrate was evaporated at <40° C., yielding 18.5 parts (100%) of 4-[1-(1H-imidazol-1-yl)ethyl]-N$^2$-methyl-1,2-benzenediamine as a residue (int. 97).

In a similar manner there were also prepared:
4-[(1H-imidazol-1-yl)phenylmethyl]-N$^1$-methyl-1,2-benzenediamine as a residue (int. 98);
4-[1-(1H-imidazol-1-yl)-2-methylpropyl]-N$^1$-methyl-1,2-benzenediamine as a residue (int. 99); and
4-[1-(1H-imidazol-1-yl)ethyl]-N$^1$-(phenylmethyl)-1,2-benzenediamine as a residue (int. 100).

Example 9

(a-1) To a stirred and refluxed Grignard complex previously prepared starting from 110.7 parts of 2-bromopropane, 21.75 parts of magnesium and 900 parts of dry tetrahydrofuran were added dropwise 50 parts of N-(4-formylphenyl)acetamide at <30° C. Upon completion, stirring was continued for 1 hour at room temperature. The reaction mixture was hydrolysed with a mixture of ammonium chloride and crushed ice and the product was extracted with ethyl acetate. The extract was washed with water, dried, filtered and evaporated to dry, yielding 63.5 parts (100%) of N-[4-(1-hydroxy-2-methylpropyl)phenyl]acetamide as a residue (int. 101).

(a-2) A mixture of 10.4 parts of N-[4-(1-hydroxy-2-methylpropyl)phenyl]acetamide, 16 parts of 1,1'-carbonylbis[1H-imidazole] and 90 parts of tetrahydrofuran was stirred for 12 hours at room temperature. After evaporation to dry, the residue was taken up in water and treated with ammonium hydroxide. The product was extracted with trichloromethane. The extract was dried, filtered and evaporated. The residue was purified by column chromatography over silica gel using a mixture of trichloromethane and methanol (98:2 by volume) as eluent. The pure fractions were collected and the eluent was evaporated, yielding 6.8 parts (53%) of N-[4-[1-(1H-imidazol-1-yl)-2-methylpropyl]-phenylacetamide; mp. 244° C. (int. 102).

(a-3) To a stirred and cooled (0° C.) mixture of 21.5 parts of N-[4-[1-(1H-imidazol-1-yl)-2-methylpropyl]-phenyl]acetamide and 183 parts of concentrated sulfuric acid were added portionwise 8.6 parts of potassium nitrate at 0°~5° C. The reaction mixture was poured into ice water and treated with ammonium hydroxide. The product was extracted three times with 150 parts of trichloromethane. The combined extracts were dried, filtered and evaporated, yielding 20 parts (80%) of N-[4-[1(1H-imidazol-1-yl)-2-methylpropyl]-2-nitrophenyl]acetamide as a residue (int. 103).

(a-4) A mixture of 56 parts of 4-[1-(1H-imidazol-1-yl)-2-methylpropyl]-2-nitrobenezenamine and 300 parts of a hydrochloric acid solution 3N was stirred for 1 hour at reflux temperature. After cooling, the reaction mixture was poured into 1000 parts of ice water and treated with ammonium hydroxide. The product was extracted three times with 150 parts of trichloromethane. The combined extracts were dried, filtered and evaporated, yielding 31 parts (64%) of 4-[1-(1H-imidazol-1-yl)-2-methylpropyl]-2-nitrobenzenamine (int. 104).

(a-5) A mixture of 31 parts of 4-[1-(1H-imidazol-1-yl)-2-methylpropyl]-2-nitrobenzenamine and 240 parts of ethanol was hydrogenated at room temperature in a Parr apparatus at 0.5 10$^5$Pa with 30 parts of Raney-nickel catalyst. After the calculated amount of hydrogen was taken up, the catalyst was filtered off over diatomaceous earth and the filtrate was evaporated, yielding 27.4 parts (99.9%) of 4-[1-(1H-imidazol-1-yl)-2-methylpropyl]-1,2-benzenediamine as a residue (int. 105).

In a similar manner there were also prepared:
4-(1H-imidazol-1-ylmethyl)-1,2-benzenediamine as a residue (int. 106);
4-[1-(1H-imidazol-1-yl)ethyl]-1,2-benzenediamine as an oil (int. 107);
4-[1-(1H-imidazol-1-yl)-3-methylbutyl]-1,2-benzenediamine (int. 108);
4-[1-(1H-imidazol-1-yl)propyl]-1,2-benzenediamine as a residue (109);
4-[1-(1H-imidazol-1-yl)heptyl]-1,2-benzenediamine (int. 110); and
4-[1-(1H-imidazol-1-yl)butyl]-1,2-benzenediamine as a residue (111).

Example 10

(a-1) To a stirred solution of 50.2 parts of α-methyl-4-nitrobenzenemethanol and 48.6 parts of N,N-diethylethanamine in 390 parts of dry dichloromethane was added dropwise a solution of 37.8 parts of methanesulfonyl chloride in 65 parts of dry dichloromethane at −5~0° C. The whole was stirred for 1 hour at 0° C. 75 Parts of cold water were added and the dichloromethane layer was decanted, dried, filtered and evaporated. The residue was purified by column chromatography over silica gel using trichloromethane as eluent. The pure fractions were collected and the eluent was evaporated. The solid residue was shaked with 2,2'-oxybispropane. The product was filtered off and dried, yielding 67.1 parts (91%) of [1-(4-nitrophenyl)ethyl] methanesulfonate; mp. 70° C. (int. 112).

(a-2) A mixture of 37.5 parts of 1H-imidazole, 61.3 parts of [1-(4-nitrophenyl)ethyl] methanesulfonate and 200 parts of acetonitrile was stirred and refluxed for 2.50 hours. After cooling, the whole was filtered and the filtrate was evaporated. 150 Parts of water were added and the product was extracted three times with 130 parts of dichloromethane. The combined extracts were dried, filtered and evaporated. The residue was purified by column chromatography over silica gel using a mixture of trichloromethane and methanol (95:5 by volume) as eluent. The pure fractions were collected and the eluent was evaporated, yielding 34.4 parts (63.3%) of 1-[1-(4-nitrophenyl)ethyl]-1H-imidazole as a solid residue (int. 113).

(a-3) A mixture of 34.4 parts of 1-[1-(4-nitrophenyl)ethyl]-1H-imidazole, 2 parts of a solution of thiophene in methanol 4%, 200 parts of methanol and 200 parts of methanol saturated with ammonia was hydrogenated at normal pressure and at room temperature with 4 parts of platinum-on-charcoal catalyst 5%. After the calculated amount of hydrogen was taken up, the catalyst was filtered off and the filtrate was evaporated. The oily residue was crystallized from a mixture of 2-propanol and 2,2'-oxybispropane (2:1 by volume). The product was filtered off and dried, yielding 27 parts (91.3%) of 4-[1-(1H-imidazol-1-yl)ethyl]benzenamine; mp. 130° C. (int. 114).

(a-4) To a stirred solution of 15 parts of 4-[1-(1H-imidazol-1-yl)ethyl]-benzenamine and 2.7 parts of sodium formate in 60 parts of formic acid is added dropwise a solution of 9 parts of acetic acid anhydride in 24 parts of formic acid at 50° C. The reaction mixture was stirred for 1 hour at 100° C. and the solvent was evaporated. The residue was dissolved in a small amount of ice water and the solution was treated with ammonium hydroxide while cooling. The product was extracted twice with dichloromethane. The combined extracts were dried, filtered and evaporated. The residue was crystallized twice from tetrahydrofuran, yielding 13.8 parts (80%) of N-[4-[1-(1H-imidazol-1-yl)ethyl]phenyl]formamide; mp. 129.4° C. (int. 115).

(a-4) To a cooled and stirred solution of 13 parts of N-[4-[1-(1H-imidazol-1-yl)ethyl]phenyl]formamide in 92 parts of concentrated sulfuric acid was added portionwise 6.1 parts of potassium nitrate at a temperature between −5° to −10° C. Upon completion, stirring was continued for 1.50 hour at 0° C. The reaction mixture was poured into crushed ice. The whole was treated with ammonium hydroxide at 0°~−10° C. The product was extracted three times with 195 parts of dichloromethane. The extract was dried, filtered and evaporated. The residue was crystallized from 48 parts of 2-propanol. The product was filtered off and dried, yielding 5.4 parts (34.6%) of N-[4-[1-(1H-imidazol-1-yl)-ethyl]-2-nitrophenyl]formamide; mp. 158° C. (int. 116).

In a similar manner there were also prepared:
N-[4-(1H-imidazol-1-ylmethyl)-2-nitrophenyl]acetamide (int. 117);
N-[4-[1-(1H-imidazol-1-yl)ethyl]-2-nitrophenyl]acetamide (int. 118);
N-[3-(1H-imidazol-1-ylmethyl)-2-nitrophenyl]acetamide; mp. 182.1° C. (int. 119); and
N-[5-(1H-imidazol-1-ylmethyl)-2-nitrophenyl]acetamide; mp. 136.0° C. (120).

(b-1) A mixture of 5.4 parts of N-[4-[1-(1H-imidazol-1-yl)ethyl]-2-nitrophenyl]formamide, 1 part of a solution of thiophene in methanol 4% and 200 parts of methanol was hydrogenated at normal pressure and at 50° C. with 2 parts of platinum-on-charcoal catalyst 5%. After the calculated amount of hydrogen was taken up, the catalyst was filtered off and the filtrate was evaporated, yielding 5 parts (100%) of
N-[2-amino-4-[1-(1H-imidazol-1-yl)ethyl]phenyl]formamide (int. 121).

In a similar manner there were also prepared:
N-[2-amino-4-(1H-imidazol-1-ylmethyl)phenyl]acetamide as a solid residue (int. 122); and N-[2-amino-4-[1-(1H-imidazol-1-yl)ethyl]phenyl]acetamide; mp. 211.7° C. (int. 123).

Example 11

(a-1) To a stirred and cooled (water-bath) mixture of 48.5 parts of (4-amino-3-nitrophenyl)phenylmethanone and 320 parts of methanol were added portionwise 11.4 parts of sodium tetrahydroborate. Upon completion, stirring was continued for 15 minutes at room temperature. 100 Parts of water were added and the methanol was evaporated. The precipitated product was filtered off, washed with water, dried, filtered and crystallized twice from a moisture of methanol and water, yielding 19.6 parts of 4-amino-3-nitro-α-phenylbenzenemethanol; mp. 125° C. (int. 124).

(a-2) To a stirred solution of 7.5 parts of 4-amino-3-nitro-α-phenylbenzenemethanol, 0.1 parts of a sodium hydride dispersion 50% and 90 parts of tetrahydrofuran were added 6.4 parts of 1,1'-carbonylbis-[1H-imidazole]. The whole was stirred and refluxed for 1 hour. The reaction mixture was evaporated. The residue was purified by column chromatography over silica gel using a mixture of trichloromethane and methanol (93:7 by volume) as eluent. The pure fractions were collected and the eluent was evaporated. The residue was crystallized from 180 parts of methylbenzene, yielding, after melting at 80° C. for 2 hours, 6.33 parts (71%) of 4-[(1H-imidazol-1-yl)phenylmethyl]-2-nitrobenzenamine (int. 125).

(a-3) A mixture of 3.4 parts of 4-[(1H-imidazol-1-yl)phenylmethyl]-2-nitrobenzenamine, 1 part of a solution of thiophene in methanol 4%, 80 parts of methanol and 80 parts of methanol saturated with ammonia was hydrogenated at normal pressure and at room temperature with 2 parts of platinum-on-charcoal catalyst 5%. After the calculated amount of hydrogen was taken up, the catalyst was filtered off and the filtrate was evaporated, yielding 2.64 parts (99%) of 4-[(1H-imidazol-1-yl)-phenylmethyl]-1,2-benzenediamine as a residue (int. 126), or alternatively (a-4) A mixture of 1.45 parts of 4-[(1H-imidazol-1-yl)phenylmethyl]-2-nitrobenzenamine, 0.78 parts of acetyl chloride and 25 parts of acetic acid was stirred over weekend at room temperature. The methanol layer was removed in vacuo and the residue was taken up in water and dichloromethane. After treatment with ammonium hydroxide, the dichloromethane layer was dried, filtered and evaporated, yielding 1.6 parts (95%) of N-[4-[(1H-imidazol-1-yl)phenylmethyl]-2-nitrophenyl]-acetamide as a residue (int. 127).

In a similar manner there were also prepared:

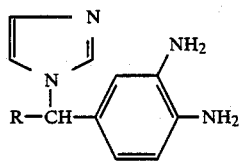

| No. | R |
|---|---|
| 128 | 3-pyridinyl |
| 129 | 1H—imidazol-1-yl |
| 130 | 2-thienyl |
| 131 | 4-fluorophenyl |
| 132 | 2,4-dichlorophenyl |
| 133 | 3-chlorophenyl |
| 134 | 3,4-dichlorophenyl |
| 135 | 3-methylphenyl |
| 136 | cyclopropyl |
| 137 | 4-methoxyphenyl |
| 138 | n-butyl |

Example 12

(a-1) To a stirred solution of 110 parts of (±)-4-amino-3-nitro-α-phenylbenzenemethanamine in 880 parts of methanol was added a solution of 68.4 parts of (−)-[S(R*,R*)]-2,3-dihydroxybutanedioic acid in 544 parts of methanol. The crystallized product was filtered off and recrystallized twice from a mixture of methanol and water (85:15 by volume). The product was filtered off and derivated with 2,3,4,6-tetraacetate-α,D-glucopyranosyl isocyanide. The product was filtered off and dried, yielding 26 parts (14.4%) of (+)-4-amino-3-nitro-α-phenylbenzenemethanamine (−)-[S(R*,R*)]-2,3-dihydroxybutanedioic acid (139).

(a-2) From (+)-4-amino-3-nitro-α-phenylbenzenemethanamine (−)-[S(R*,R*)]-2,3-dihydroxybutanedioic acid, the base was liberated in the conventional manner with water, ammonium hydroxide and dichloromethane. The extracts were dried, filtered and evaporated. A mixture of the residue, 8.6 parts of 2-isothiocyanato-1,1-dimethoxyethane and 80 parts of methanol was stirred for 1.5 hour at reflux temperature. After cooling, the reaction mixture was evaporated. The residue was purified by column chromatography over silica gel using a mixture of trichloromethane and methanol (99:1 by volume) as eluent. The pure fractions were collected and the eluent was evaporated, yielding 22.3 parts (98.3%) of (+)-N-[(4-amino-3-nitrophenyl)phenylmethyl]-N'-(2,2-dimethoxyethyl)thiourea as a residue (int. 140).

(a-3) A mixture of 22.3 parts of (+)-N-[(4-amino-3-nitrophenyl)phenylmethyl]-N'-(2,2-dimethoxyethyl)thiourea, 10.2 parts of iodomethane, 11.8 parts of potassium carbonate and 240 parts of 2-propanone was stirred over weekend at room temperature. The reaction mixture was filtered over diatomaceous earth and the filtrate was evaporated. The residue was purified by column chromatography over silica gel using a mixture of trichloromethane and methanol (98:2 by volume) as eluent. The pure fractions were collected and the elunet was evaporated, yielding 23 parts (100%) of (+)-methyl N-[(4-amino-3-nitrophenyl)phenylmethyl]-N'-(2,2-dimethoxyethyl)carbamimidothioate as a residue (141).

(a-4) A mixture of 23 parts of (+)-methyl N-[(4-amino-3-nitrophenyl)phenylmethyl]-N'-(2,2-dimethoxyethyl)carbamimidothioate and 450 parts of concentrated sulfuric acid was stirred for 1 hour while cooling in an ice bath. The reaction mixture was poured into crushed ice and treated with an ammonium hydroxide solution. The product was extracted three times with trichloromethane. The combined extracts were dried, filtered and evaporated. The residue was purified by column chromatography over silica gel using a mixture of trichloromethane and methanol (98:2 by volume) as eluent. The pure fractions were collected and the eluent was evaporated. The residue was converted into the hydrochloride salt in 2-propanol. The salt was filtered off and crystallized from methanol. The product was filtered off and dried, yielding 5.5 parts (25.6%) of (+)-4-[[2-(methylthio)-1H-imidazol-1-yl]phenylmethyl]-2-nitrobenzenamine monohydrochloride (int. 142).

(a-5) A mixture of 5.5 parts of (+)-4-[[2-(methylthio)-1H-imidazol-1-yl]-phenylmethyl]-2-nitrobenzenamine monohydrochloride, 24 parts of concentrated hydrochloric acid, 2 parts of a solution of thiophene in methanol 4%, 120 parts of methanol and 100 parts of water was hydrogenated at normal pressure and at 0° C. with 2 parts of palladium-on-charcoal catalyst 10%. After the calculated amount of hydrogen was taken up, the catalyst was filtered off and the filtrate was evaporated. The residue was taken up in water and treated with an ammonium hydroxide solution. The product was extracted three times with dichloromethane. The combined extracts were dried, filtered and evaporated, yielding 5.6 parts (100%) of (+)-4-[[2-(methylthio)-1H- imidazol-1-yl]phenylmethyl]-1,2-benzendiamine as a residue (int. 143).

(a-6) A mixture of 5.6 parts of (+)-4-[[2-(methylthio)-1H-imidazol-1-yl]-phenylmethyl]-1,2-benzendiamine, 2.8 parts of ethyl ethanimidate hydrochloride and 60 parts of methanol was stirred first overnight at room temperature and then for 2 hours at reflux temperature. After cooling, the reaction mixture was evaporated. The residue was treated with alkaline water and the product was extracted three times with dichloromethane. The combined extracts were dried, filtered and evaporated. The residue was purified by column chromatography over silica gel using a mixture of dichloromethane and methanol (96:4 by volume) as eluent. The pure fractions were collected and the eluent was evaporated, yielding 3.2 parts (79.3%) of (+)-2-methyl-5-[[2-(methylthio)-1H-imidazol-1-yl]phenylmethyl]-1H-benzimidazole as a residue (int. 144).

In a similar manner there was also prepared:
(−)-2-methyl-5-[[2-(methylthio)-1H-imidazol-1-yl]phenylmethyl]-1H-benzimidazole as a residue (int. 145).

B. Preparation of final compounds

Example 13

A mixture of 6.8 parts of 1H-imidazole, 4.9 parts of 5-(chloromethyl)-2-ethyl-1-methyl-1H-benzimidazole monohydrochloride and 80 parts of acetonitrile was stirred and refluxed for 3 hours. The reaction mixture was evaporated. The residue was purified by column chromatography over silica gel using a mixture of trichloromethane and methanol (95:5 by volume) as eluent. The pure fractions were collected and the eluent was evaporated. The residue was crystallized from ethyl acetate. The product was filtered off, washed with 2,2'-oxybispropane and dried, yielding 2.6 parts (54%) of 2-ethyl-5-(1H-imidazol-1-yl-methyl)-1-methyl-1H-benzimidazole; mp. 127.3° C. (compound 1).

In a similar manner there were also prepared:

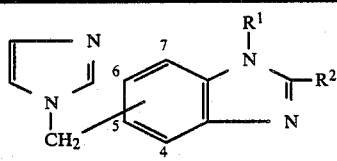

| No. | R$^1$ | R$^2$ | salt/base | position | mp (°C.) |
|---|---|---|---|---|---|
| 2 | n-C$_3$H$_7$ | CH$_3$ | 1 ½ (COOH)$_2$ | 5 | 194.6 |
| 3 | CH$_3$ | CH$_3$ | base | 5 | 185.3 |
| 4 | H | CH$_3$ | base | 5 | 158.3 |
| 5 | n-C$_3$H$_7$ | H | base | 5 | 100.9 |
| 6 | n-C$_3$H$_7$ | C$_6$H$_5$ | base | 5 | 115.5 |
| 7 | H | C$_2$H$_5$ | base | 5 | 174.2 |
| 8 | CH$_3$ | n-C$_3$H$_7$ | base | 5 | 113.2 |
| 9 | H | C$_6$H$_5$ | 2 HCl | 5 | 283.8 |
| 10 | H | n-C$_3$H$_7$ | 2 (COOH)$_2$·½ H$_2$O | 5 | 132.0 |
| 11 | CH$_3$ | C$_6$H$_5$ | 2 (COOH)$_2$ | 5 | 168.4 |
| 12 | n-C$_3$H$_7$ | C$_2$H$_5$ | 2 HCl.H$_2$O | 5 | 141.5 |
| 13 | n-C$_3$H$_7$ | 3-pyridinyl | 3 (COOH)$_2$.H$_2$O | 5 | 119.1 |
| 14 | H | C$_6$H$_5$ | base | 5 | 218.4 |
| 15 | OCH$_3$ | H | 2 HCl.H$_2$O | 6 | 163.3 |
| 16 | H | H | 2 HCl | 4 | 267.9 |
| 17 | H | 3-pyridinyl | 3 HCl | 4 | 261.0 |
| 18 | H | C$_6$H$_5$ | base | 4 | 229.8 |
| 19 | CH$_3$ | H | base | 5 | 135.2 |
| 20 | CH$_3$ | CF$_3$ | base | 5 | 124.8 | and 5-[(3-fluorophenyl)(1H-imidazol-1-yl)methyl]-2-methyl-1H-benzimidazole; mp. 128.8° C. (compound 21); and 5-[(3-fluorophenyl)(1H-imidazol-1-yl)methyl]-1H-benzimidazole; mp. 85.6° C. (compound 22).

Example 14

A mixture of 7.5 parts of 1H-imidazole, 12.6 parts of 2-methyl-α-phenyl-1H-benzimidazole-5-methanol methanesulfonate(ester) and 80 parts of acetonitrile was stirred and refluxed for 18 hours. The reaction mixture was evaporated. Water was added and the oily layer was separated and dissolved in trichloromethane. It was dried, filtered and evaporated. The residue was purified twice by column chromatography over silica gel using a mixture of trichloromethane, methanol and methanol, saturated with ammonia, (90:5:5 by volume) as eluent. The pure fractions were collected and the eluent was evaporated. The residue was further purified by reversed phase chromatography (HPLC) using a mixture of 60% of methanol containing 0.8% of N-(1-methylethyl)-2-propanamine and 40% of water containing 0.5% of ammonium acetate. The pure fractions were collected and the eluent was evaporated, yielding, after drying in vacuo for 12 hours at 95° C., 1.8 parts (15%) of 5-[(1H-imidazol-1-yl)phenylmethyl]-2-methyl-1H-benzimidazole; mp. 118.4° C. (compound 23).

Example 15

A mixture of 6.35 parts of 5-(chloromethyl)-1,3-dihydro-2H-benzimidazol-2-one, 11.9 parts of 1H-imidazole and 135 parts of N,N-dimethylformamide was stirred overnight at 80° C. The whole was evaporated. The residue was purified by column chromatography over silica gel using a mixture of trichloromethane and methanol (80:20 by volume) as eluent. The pure fractions were collected and the eluent was evaporated. After standing over weekend at room temperature, the residue was solidified. The product was pulverized and stirred in acetonitrile. The product was filtered off and purified by column chromatography over silica gel using a mixture of trichloromethane and methanol (87:13 by volume) as eluent. The pure fractions were collected and the eluent was evaporated. The residue was dried in a dry-pistol at 130° C., yielding 0.75 parts (10%) of 1,3-dihydro-5-(1H-imidazol-1-ylmethyl)-2H-benzimidazol-2-one; mp. 254.5° C. (compound 24).

Example 16

A mixture of 2.8 parts of 1-methoxy-2-methyl-α-phenyl-1H-benzimidazole-5-methanol, 1.95 parts of 1,1'-carbonylbis[1H-imidazole] and 72 parts of tetrahydrofuran was stirred for 17 hours at reflux temperature. After evaporation, the residue was purified by column chromatography over silica gel using a mixture of trichloromethane and methanol (90:10 by volume) as eluent. The pure fractions were collected and the eluent was evaporated. The residue was further purified twice by column chromatography over silica gel using a mixture of trichloromethane and methanol (95:5 by volume) as eluent. The pure fractions were collected and the eluent was evaporated, yielding 2 parts (59.8%) of 5-[(1H-imidazol-1-yl)phenylmethyl]-1-methoxy-2-methyl-1H-benzimidazole as a residue (compound 25).

In a similar manner there were also prepared:

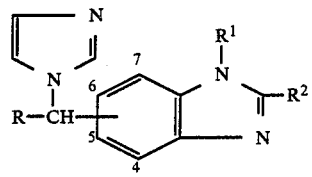

| No. | R | R¹ | R² | base salt | position | mp. (°C.) |
|---|---|---|---|---|---|---|
| 26 | C₆H₅ | OCH₃ | C₆H₅ | base | 6 | 113.4 |
| 27 | C₆H₅ | OCH₃ | C₆H₅ | base | 5 | 164.0 |
| 28 | C₆H₅ | CH₃ | H | base | 5 | 138.7 |
| 29 | C₆H₅ | CH₃ | CH₃ | base | 6 | 132.1 |
| 30 | C₆H₅ | CH₃ | C₆H₅ | base | 6 | 162.1 |
| 31 | 2-thienyl | H | C₆H₅ | base | 5 | 183.0 |
| 32 | C₆H₅ | OCH₃ | H | base | 6 | — |
| 33 | C₆H₅ | H | CH₃ | 2(COOH)₂.H₂O | 4 | 63.5 |
| 34 | 2-thienyl | H | 4-thiazolyl | base | 5 | 188.0 |
| 35 | H | H | CH₃ | base | 4 | 139.9 |
| 36 | 5-bromo-2-furanyl | H | H | 1½(COOH)₂ | 5 | 116.3 |
| 37 | 2-furanyl | H | H | base | 5 | 150.9 |

Example 17

A mixture of 3 parts of 1-methoxy-α,2-dimethyl-1H-benzimidazole-6-methanol, 2.73 parts of 1,1'-carbonylbis[1H-imidazole] and 90 parts of tetrahydrofuran was stirred for 17 hours at reflux temperature. The tetrahydrofuran layer was evaporated in vacuo and the residue was taken up in 90 parts of methylbenzene. After stirring for 3 hours at reflux temperature, the mixture was evaporated and the residue was purified twice by column chromatography over silica gel using a mixture of trichloromethane and methanol (90:10 by volume) as eluent. The pure fractions were collected and the eluent was evaporated. The residue was dried in vacuo, yielding 1.2 parts (32.0%) of 6-[1-(1H-imidazol-1-yl)ethyl]-1-methoxy-2-methyl-1H-benzimidazole as an oily residue (compound 38).

Example 18

A mixture of 9 parts of 4-[1-(1H-imidazol-1-yl)heptyl]-1,2-benzenediamine, 5 parts of 4-fluorobenzoic acid and 100 parts of polyphosphoric acid was stirred for 2 hours at 100° C. After cooling, the reaction mixture was poured into ice water and treated with ammonium hydroxide. The product was extracted three times with 120 parts of trichloromethane. The combined extracts were dried, filtered and evaporated. The residue was purified by column chromatography over silica gel using a mixture of trichloromethane and methanol (98:2 by volume) as eluent. The pure fractions were collected and the eluent was evaporated. The residue was crystallized from a mixture of 2-propanone and 1,1'-oxybisethane. The product was filtered off and dried, yielding 5.8 parts (47%) of 2-(4-fluorophenyl)-5-[1-(1H-imidazol-1-yl)heptyl]-1H-benzimidazole; mp. 121.9° C. (compound 39).

In a similar manner there were also prepared:

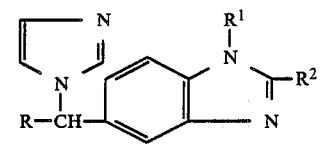

| No. | R | R¹ | R² | salt/base | mp (°C.) |
|---|---|---|---|---|---|
| 40 | H | H | (3-pyridinylmethyl) | 3 HCl | 254.5 |
| 41 | H | H | 2-CH₃O—C₆H₄ | base | 185.3 |
| 42 | H | H | 3-CH₃O—C₆H₄ | base | 169.7 |
| 43 | H | H | (2-pyridinylmethyl) | 3 HCl.½ H₂O | 222.2 |
| 44 | H | H | n-C₆H₁₃ | 2 (COOH)₂.½ H₂O | 101.8 |
| 45 | H | H | (4-pyridinyl)CH=CH | base.E-form | 234.1 |
| 46 | H | H | (3-pyridinyl)CH=CH | 3 HCl.H₂O | 270.3 |
| 47 | H | H | 2-thienyl | base | 196.4 |
| 48 | H | H | (1H—imidazol-5-yl)-CH=CH | 3 HCl.1½ H₂O | 237.0 |
| 49 | C₆H₅ | H | 4-CH₃O—C₆H₄ | base | 236.5 |
| 50 | H | H | 2-CH₃—C₆H₄ | 2 (COOH)₂ | 176.0 |
| 51 | H | H | 4-thiazolyl | 2 HCl.2 H₂O | 147.6 |
| 52 | H | H | 3-quinolinyl | base | >300 |
| 53 | H | H | 2-NH₂—3-pyridinyl | base | 267.5 |
| 54 | C₂H₅ | H | C₆H₅ | base | 203.7 |
| 55 | C₂H₅ | H | 4-F—C₆H₄ | base | 197.4 |
| 56 | i-C₄H₉ | H | 4-F—C₆H₄ | base | 187.9 |
| 57 | n-C₄H₉ | H | C₆H₅ | base | 153.4 |
| 58 | CH₃ | H | 4-F—C₆H₄ | base | 191.1 |
| 59 | i-C₄H₉ | H | C₆H₅ | 1½ (COOH)₂.½ H₂O | 105.5 |
| 60 | CH₃ | H | C₆H₅ | base | 196.2 |
| 61 | n-C₄H₉ | H | 4-F—C₆H₄ | base | 163.8 |
| 62 | CH₃ | CH₃ | C₆H₅ | 2 (COOH)₂ | 144.6 |
| 63 | CH₃ | CH₃ | 4-F—C₆H₄ | 2 (COOH)₂ | 151.0 |

Example 19

A mixture of 3.6 parts of 4-[1-(1H-imidazol-1-yl)ethyl]-1,2-benzenediamine, 5 parts of trifluoroacetic acid and 100 parts of a hydrochloric acid solution 4N was stirred for 6 hours at reflux temperature. The reaction mixture was concentrated and the concentrate was dissolved in 50 parts of water. The mixture was made alkaline with sodium hydrogen carbonate and the product was extracted with dichloromethane. The extract was dried, filtered and concentrated. The concentrate was purified by column chromatography over silica gel using a mixture of trichloromethane and methanol (97.5:2.5 by volume) as eluent. The pure fractions were collected and the eluent was concentrated. The concentrate was crystallized from 20 parts of ethyl acetate. The product was filtered off and dried, yielding 3.4 parts (69.3%) of 5-[1-(1H-imidazol-1-yl)ethyl]-2-(trifluoromethyl)-1-H-benzimidazole; mp. 164.6° C. (compound 64).

In a similar manner there were also prepared:

| No. | R | R¹ | R² | salt/base | mp (°C.) |
|---|---|---|---|---|---|
| 65 | H | H | CH₂OH | 2 HCl | 241.3 |
| 66 | H | H | n-C₄H₉ | 2 HCl | 237.5 |
| 67 | H | H | CF₃ | base | 206.0 |
| 68 | H | n-C₃H₇ | CH₂OH | 2 (COOH)₂ | 134.3 |
| 69 | H | H | 2-thienylmethyl | base | 174.3 |
| 70 | H | H | 2-thienylmethyl | base | 145.4 |
| 71 | H | H | 1H—indol-3-ylmethyl | base | 124.5 |

-continued

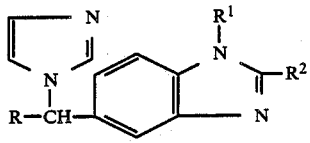

| No. | R | R¹ | R² | salt/base | mp (°C.) |
|-----|-----|-----|-----|-----|------|
| 72 | H | H | 2-thienyl-n-propyl | 2 HCl | 220.1 |
| 73 | H | H | 3-furanyl | base | 202.8 |
| 74 | $C_6H_5$ | H | $C_2H_5$ | base | 108.1 |
| 75 | $C_6H_5$ | H | $CF_3$ | base | 194.3 |
| 76 | $C_6H_5$ | $CH_3$ | $CF_3$ | base | 86.3 |
| 77 | $C_6H_5$ | $CH_3$ | $CH_3$ | base | 187.6 |
| 78 | $CH_3$ | H | $CHF_2$ | base | 140.5 |
| 79 | $C_6H_5$ | H | $CH(OH)-C_6H_5$ | base | 260.6 |
| 80 | H | $CH_3$ | $CH_2-OH$ | 2HCl.½ $H_2O$ | 216.3 |
| 81 | $CH_3$ | H | $CH_2-OH$ | base | 152 |

Example 20

A mixture of 10 parts of 4-(1H-imidazol-1-ylmethyl)-1,2-benzenediamine, 8 parts of 1,3-isobenzofurandione and 80 parts of a hydrochloric acid solution 3N was stirred for 4 hours at reflux temperature. After cooling, the mixture was treated with a sodium hydroxide solution 3N to pH 5.5. The reaction mixture was evaporated to dry. The residue was taken up in ethanol at 60° C. The mixture was filtered while hot and the filtrate was evaporated to dry. The residue was purified by column chromatography over silica gel using a mixture of trichloromethane and methanol (70:30 by volume) as eluent. The pure fractions were collected and the eluent was evaporated. The residue was converted into the hydrochloride salt in 2-propanol, water and 1,1'-oxybisethane. The mixture was evaporated and the residue was solidified on scratching in 30 parts of a mixture of 2-propanol and 2-propanone. The product was filtered off and dried, yielding 2.4 parts (10.5%) of 2-[5-(1H-imidazol-1-ylmethyl)-1H-benzimidazol-2-yl]benzoic acid dihydrochloride,dihydrate; mp. 245.0° C. (compound 82).

Example 21

A mixture of 6.1 parts of 4-[1-(1H-imidazol-1-yl)propyl]-1,2-benzenediamine and 90 parts of trifluoroacetic acid was stirred for 15 minutes at 80° C. The reaction mixture was poured into crushed ice and treated with ammonium hydroxide. The product was extracted with trichloromethane. The extract was dried, filtered and evaporated. The residue was purified by column chromatography over silica gel using a mixture of trichloromethane, methanol and ammonium hydroxide (90:10:1 by volume) as eluent. The pure fractions were collected and the eluent was evaporated. The residue was crystallized from a mixture of 2-propanone and 2,2'-oxybispropane (4 parts—17.5 parts). The product was filtered off and dried, yielding 1.8 parts (22%) of 5-[1-(1H-imidazol-1-yl)propyl]-2-(trifluoromethyl)-1H-benzimidazole; mp. 173.2° C. (compound 83).

In a similar manner there were also prepared:

5-[1-(1H-imidazol-1-yl)-2-methylpropyl]-2-(trifluoromethyl)-1H-benzimidazole ethanedioate(1:1).hemihydrate; mp. 106.2° C. (compound 84);

5-[1-(1H-imidazol-1-yl)heptyl]-2-(trifluoromethyl)-1H-benzimidazole ethanedioate(2:3).hemihydrate; mp. 96.2° C. (compound 85);

5-[1-(1H-imidazol-1-yl)heptyl]-1H-benzimidazole ethanedioate(1:1); mp. 210.7° C. (compound 86); and 5-[1-(1H-imidazol-1-yl)ethyl]-1-methyl-1H-benzimidazole ethanedioate (2:5); mp. 166.5° C. (compound 87).

Example 22

A mixture of 5 parts of 4-(1H-imidazol-1-ylmethyl)-1,2-benzenediamine, 5 parts of ethyl 2-chlorobenzoate and 30 parts of polyphosphoric acid was stirred for 4 hours at 140° C. The whole was poured into 200 parts of water and crushed ice. The mixture was treated with ammonium hydroxide. The product was extracted three times with 120 parts of trichloromethane. The combined extracts were dried, filtered and evaporated. The residue was purified by column chromatography (HPLC) over silica gel using a mixture of trichloromethane, methanol and ammonium hydroxide (90:10:0.05 by volume) as eluent. The pure fractions were collected and the eluent was evaporated. The residue was crystallized from a mixture of 2-propanone and 1,1'-oxybisethane. The product was filtered off and dried in vacuo at 100° C., yielding 2.1 parts (26%) of 2-(2-chlorophenyl)-5-(1H-imidazol-1-ylmethyl)-1H-benzimidazole; mp. 115.2° C. (compound 88).

In a similar manner there were also prepared:

2-(4-chlorophenyl)-5-(1H-imidazol-1-ylmethyl)-1H-benzimidazole dihydrochloride.hemihydrate; mp. 287.1° C. (compound 89);

2-(4-chlorophenyl)-5-[(1H-imidazol-1-yl)phenylmethyl]-1H-benzimidazole; mp. 236.3° C. (compound 90);

2-(2-fluorophenyl)-5-(1H-imidazol-1-ylmethyl)-1H-benzimidazole hemihydrate; mp. 156.1° C. (compound 91); and 2-(2-fluorophenyl)-5-[(1H-imidazol-1-yl)phenylmethyl]-1H-benzimidazole ethanedioate(2:3); mp. 112.5° C. (compound 92).

Example 23

A mixture of 2.99 parts of 4-[(3-chlorophenyl)(1H-imidazol-1-yl)methyl]-1,2-benzenediamine, 50 parts of trimethoxymethane and 2.4 parts of formic acid was stirred for 16 hours at room temperature. The reaction mixture was evaporated. The residue was dissolved in hydrochloric acid solution 2N. This solution was treated with ammonia and the product was extracted with dichloromethane. The extract was dried, filtered and evaporated. The residue was purified by column chromatography over silica gel using a mixture of trichloromethane, methanol and methanol, saturated with ammonia, (90:5:5 by volume) as eluent. The pure fractions were collected and the eluent was evaporated, yielding 1.8 parts (58.2%) of 5-[(3-chlorophenyl)(1H-imidazol-1-yl)methyl]-1H-benzimidazole; mp. 108.2° C. (compound 93).

In a similar manner there were also prepared:

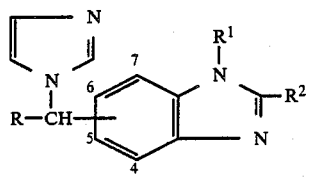

| No. | R | R¹ | salt/ R² base | position | mp (°C.) |
|---|---|---|---|---|---|
| 94 | H | H | H base | 5 | 198.3 |
| 95 | 4-F—C₆H₅ | H | H base | 5 | 104.3 |
| 96 | 1H—imidazol-1-yl | H | H base | 5 | 74.2 |
| 97 | 2,4-(Cl)₂—C₆H₃ | H | H base | 5 | 121.7 |
| 98 | 3,4-(Cl)₂—C₆H₃ | H | H base | 5 | 132.6 |
| 99 | 3—CH₃—C₆H₅ | H | H base | 5 | 104.8 |
| 100 | c—C₃H₅ | H | H base | 5 | 73.5 |
| 101 | 4—CH₃O—C₆H₅ | H | H base | 5 | 111.4 |
| 102 | H | CH₂—C₆H₅ | H base | 6 | 142.9 |
| 103 | H | CH₃ | H base | 6 | 156.1 |
| 104 | H | (CH₂)₂—C₆H₅ | H 2 HCl | 6 | 269.5 |
| 105 | H | CH₂—c—C₆H₁₁ | H base | 6 | 122.5 |
| 106 | H | c—C₇H₁₃ | H base | 6 | 94.6 |

In a similar manner there are also prepared:
1-cyclohexyl-6-(1H-imidazol-1-ylmethyl)-1H-benzimidazole (compound 107);
6-(1H-imidazol-1-ylmethyl)-1-phenyl-1H-benzimidazole (compound 108); 6-(1H-imidazol-1-ylmethyl)-1-(2-thienylmethyl)-1H-benzimidazole (compound 109); and
5-[1-(1H-imidazol-1-yl)-2-phenylethyl]-1H-benzimidazole (compound 110).

Example 24

A mixture of 2.64 parts of 4-[(1H-imidazol-1-yl)phenylmethyl]-1,2-benzenediamine, 50 parts of trimethoxymethane and 1.2 parts of acetic acid was stirred and refluxed for 8 hours. The reaction mixture was evaporated in vacuo. The residue was dissolved in dilute hydrochloric acid. The solution was treated with ammonia and the product was extracted with dichloromethane. The extract was dried, filtered and evaporated. The residue was purified by column chromatography over silica gel using a mixture of trichloromethane, methanol and methanol, saturated with ammonia, (90:5:5 by volume) as eluent. The pure fractions were collected and the eluent was evaporated. The solid residue was washed with 2-propanone, yielding 1.8 parts (65%) of 5-[(1H-imidazol-1-yl)phenylmethyl]-1H-benzimidazole; mp. 186.2° C. (compound 111).

In a similar manner there were also prepared:
5-[(1H-imidazol-1-yl)(3-pyridinyl)methyl]-1H-benzimidazole; mp. 186.2° C. (compound 112);
5-[(1H-imidazol-1-yl(2-thienyl)methyl]-1H-benzimidazole; mp. 101.0° C. (compound 113); and
6-(1H-imidazol-1-ylmethyl)-1,2-dimethyl-1H-benzimidazole; mp. 139.6° C. (compound 114).

Example 25

A mixture of 2.6 parts of 4-[(1H-imidazol-1-yl)phenylmethyl]-1,2-benzenediamine, 10 parts of tetramethoxymethane, 0.6 parts of acetic acid and 6.5 parts of dichloromethane was stirred over weekend at room temperature. After evaporation, the residue was treated with ammonium hydroxide. The product was extracted with dichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was further purified by column chromatography over silica gel using a mixture of trichloromethane, methanol and methanol, saturated with ammonia, (90:5:5 by volume) as eluent. The pure fractions were collected and the eluent was evaporated. The residue was dried in vacuo, yielding 1 part (32.8%) of 5-[(1H-imidazol-1-yl)phenylmethyl]-2-methoxy-1H-benzimidazole; mp. 109.5° C. (compound 115).

Example 26

A mixture of 5.6 parts of 4-(1H-imidazol-1-ylmethyl)-N¹-(3-pyridinylmethyl)-1,2-benzenediamine, 20 parts of triethoxyethane, 2 parts of acetic acid and 200 parts of methanol was stirred for 2 hours at reflux temperature. The reaction mixture was evaporated. Methanol and methanol, saturated with ammonia, were added. The mixture was evaporated. The residue was purified by column chromatography over silica gel using a mixture of trichloromethane, methanol and methanol, saturated with ammonia, (88:10:2 by volume) as eluent. The pure fractions were collected and the eluent was evaporated. The residue was crystallized from 40 parts of 4-methyl-2-pentanone. The product was filtered off and dried, yielding 2.5 parts (41%) of 5-(1H-imidazol-1-ylmethyl)-2-methyl-1-(3-pyridinylmethyl)-1H-benzimidazole; mp. 174.0° C. (compound 116).

Following the same procedure and using equivalent amounts of the appropriate starting materials, there was also prepared:
5-(1H-imidazol-1-ylmethyl)-1-(3-pyridinylmethyl)-1H-benzimidazole; mp. 156.4° C. (compound 117).

Example 27

A mixture of 4.4 parts of 4-[1-(1H-imidazol-1-yl)-2-methylpropyl]-1,2-benzenediamine and 45 parts of methyldynetris(oxy)trisethane was stirred for 4 hours at reflux temperature. The reaction mixture was poured into 100 parts of water and the mixture was evaporated to dry. After cooling, the residue was taken up in trichloromethane. The organic layer was dried, filtered and evaporated. The residue was purified by column chromatography over silica gel using a mixture of trichloromethane and methanol (98:2 by volume) as eluent. The pure fractions were collected and the eluent was evaporated. The residue was converted into the ethanedioate salt in 16 parts of 2-butanone and 2-propanol. The salt was filtered off and crystallized from a mixture of methanol and 2-propanol. The product was filtered off and dried, yielding 2.5 parts (40%) of 5-[1-(1H-imidazol-1-yl)-2-methylpropyl]-1H-benzimidazole ethanedioate(1:1); mp. 222.0° C. (compound 118).

In a similar manner there were also prepared:
5-[1-(1H-imidazol-1-yl)propyl]-1H-benzimidazole dihydrochloride; mp. 225.5° C. (compound 119); and
5-[1-(1H-imidazol-1-yl)pentyl]-1H-benzimidazole ethanedioate(2:3); mp. 148.8° C. (compound 120).

Example 28

A mixture of 5.3 parts of 4-[1-(1H-imidazol-1-yl)-2-methylpropyl]-1,2-benzenediamine, 2.2 parts of fluoroacetamide and 80 parts of a hydrochloric acid solution 20% was stirred for 12 hours at room temperature. After cooling, the mixture was poured into ice water and the whole was treated with ammonium hydroxide. The product was extracted three times with 75 parts of trichloromethane. The combined extracts were dried, filtered and evaporated. The residue was purified by column chromatography over silica gel using a mixture of trichloromethane and methanol (95:5 by volume) as eluent. The pure fractions were collected and the eluent was evaporated. The residue was converted into the ethanedioate salt in ethanol. The salt was filtered off and crystallized from a mixture of 2-propanone and ethanol. The product was filtered off and dried, yielding 1.7 parts (20.3%) of 2-(fluoromethyl)-5-[1-(1H-imidazol-1-yl)-2-methylpropyl]-1H-benzimidazole ethanedioate (1:1); mp. 191.6° C. (compound 121).

chromatography over silica gel using a mixture of trichloromethane, methanol and methanol saturated with ammonia (90:5:5 by volume) as eluent. The pure fractions were collected and the eluent was evaporated. The residue was dried in vacuo, yielding 2.9 parts (89.8%) of 5-[(3-chlorophenyl)(1H-imidazol-1-yl)methyl]-2-methyl-1H-benzimidazole; mp. 117.1° C. (compound 122).

In a similar manner there were also prepared:

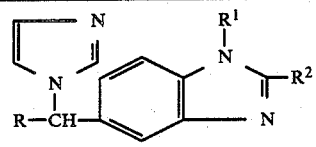

| No. | R | $R^1$ | $R^2$ | salt/base | mp (°C.) |
|---|---|---|---|---|---|
| 123 | 3-pyridinyl | H | $CH_3$ | $H_2O$ | 131.2 |
| 124 | 1H—imidazol-1-yl | H | $CH_3$ | base | 105.8 |
| 125 | 2-thienyl | H | $CH_3$ | base | 108.9 |
| 126 | 4-F—$C_6H_4$ | H | $CH_3$ | base | 110.6 |
| 127 | 2,4-$(Cl)_2$—$C_6H_3$ | H | $CH_3$ | base | 138.4 |
| 128 | 3,4-$(Cl)_2$—$C_6H_3$ | H | $CH_3$ | base | 129.3 |
| 129 | 3-$CH_3$—$C_6H_4$ | H | $CH_3$ | base | 111.1 |
| 130 | $C_6H_5$ | H | 4-pyridinyl | base | 162.0 |
| 131 | cyclopropyl | H | $CH_3$ | base | 77.0 |
| 132 | $C_6H_5$ | H | $C_6H_5$—$CH_2$ | base | 189.9 |
| 133 | H | H | n-$C_5H_{11}$ | 2HCl | 241.8 |
| 134 | $C_6H_5$ | H | n-$C_7H_{15}$ | $2\frac{1}{2}(COOH)_2$ | 144.8 |
| 135 | $C_6H_5$ | H | n-$C_8H_{17}$ | $2\frac{1}{2}(COOH)_2$ | 115.4 |
| 136 | $C_6H_5$ | H | n-$C_5H_{11}$ | $\frac{1}{2}H_2O$ | 69.9 |
| 137 | $C_6H_5$ | H | 3-F—$C_6H_4$ | 2 $(COOH)_2$ | 184.4 |
| 138 | H | H | 3-$CH_3$—$C_6H_4$ | base | 180.4 |
| 139 | H | H | 4-$CH_3$—$C_6H_4$ | base | 251.1 |
| 140 | H | H | 3-Cl—$C_6H_4$ | base | 225.8 |
| 141 | H | H | 3-F—$C_6H_4$ | base | 220.2 |
| 142 | H | H | 4-F—$C_6H_4$ | base | 231.5 |
| 143 | H | H | 2-furanyl | base | 220.9 |
| 144 | H | H | $C_6H_5$—$CH_2$ | 2HCl.$\frac{1}{2}H_2O$ | 234.0 |
| 145 | H | H | n-$C_7H_{15}$ | $2(COOH)_2.\frac{1}{2}H_2O$ | 111.1 |
| 146 | H | H | n-$C_8H_{17}$ | 2 $(COOH)_2$ | 147.1 |
| 147 | $C_6H_5$ | H | n-$C_4H_9$ | $2(COOH)_2.\frac{1}{2}H_2O$ | 98.5 |
| 148 | H | H | 4-$(C_2H_5$—O—CO)—$C_6H_4$ | base | 213.0 |
| 149 | H | H | Cl—$CH_2$ | base | — |
| 150 | $C_6H_5$ | H | cyclopropyl | base | 112.3 |
| 151 | n-$C_4H_9$ | H | $CH_3$ | base | — |
| 152 | H | H | 3-$(C_2H_5$—O—CO)—$C_6H_4$ | base | 193.2 |
| 153 | $CH_3$ | H | 4-$(C_2H_5$—O—CO)—$C_6H_4$ | base | — |
| 154 | $CH_3$ | H | n-$C_3H_7$ | $2(COOH)_2$ | 164.9 |
| 155 | n-$C_3H_7$ | H | $CH_3$ | $1\frac{1}{2}(COOH)_2$ | 174.2 |
| 156 | $CH_3$ | H | $C_2H_5$ | $2(COOH)_2$ | 214.7 |
| 157 | $CH_3$ | H | 4-$(C_2H_5$—O—CO)—$C_6H_4$ | $2(COOH)_2.H_2O$ | 169.7 |
| 158 | $C_2H_5$ | H | $C_2H_5$ | $1\frac{1}{2}(COOH)_2$.$\frac{1}{2}H_2O$ | 125.6 |
| 159 | $C_6H_5$ | H | 4-$(C_2H_5$—O—CO)—$C_6H_4$ | base | — |
| 160 | i-$C_3H_7$ | $CH_3$ | $CH_3$ | base | 232.1 |
| 161 | $CH_3$ | $CH_3$ | 4-$(C_2H_5$—O—CO)—$C_6H_4$ | base | — |
| 162 | $CH_3$ | $CH_3$ | 4-$(C_2H_5$—O—CO)—$C_6H_4$ | $2(COOH)_2.H_2O$ | — |
| 163 | $CH_3$ | $CH_2$—$C_6H_5$ | $C_6H_5$ | base | 115.1 |

Example 29

A solution of 2.99 parts of 4-[(3-chlorophenyl)(1H-imidazol-1-yl)methyl]-1,2-benzenediamine, 1.85 parts of ethyl ethanimidate hydrochloride and 40 parts of methanol was stirred for 16 hours at room temperature. The solvent was evaporated and the residue was dissolved in a dilute hydrochloric acid solution. The whole was alkalized with ammonia and the product was extracted with dichloromethane. The extract was dried, filtered and evaporated. The residue was purified by column In a similar manner there are also prepared:
1-cyclohexyl-6-(1H-imidazol-1-ylmethyl)-2-methyl-1H-benzimidazole (compound 164);
6-(1H-imidazol-1-ylmethyl)-2-methyl-1-phenyl-1H-benzimidazole (compound 165);
6-(1H-imidazol-1-ylmethyl)-2-methyl-1-(2-thienylmethyl)-1H-benzimidazole (compound 166); and
5-[1-(1H-imidazol-1-yl)-2-phenylethyl]-2-methyl-1H-benzimidazole (compound 167).

Example 30

A mixture of 3.3 parts of 4-(1H-imidazol-1-ylmethyl)-1,2-benzenediamine, 2.88 parts of ethyl cyclopropanecarboximidate hydrochloride and 64 parts of ethanol was stirred first for 4 hours at room temperature and further for 1 hour at reflux. The reaction mixture was cooled, treated with methanol, saturated with ammonia, and evaporated. The residue was purified twice by column chromatography over silica gel using first a mixture of trichloromethane and methanol (90:10 by volume) and then a mixture of trichloromethane and methanol (92:8 by volume) as eluent. The pure fractions were collected and the eluent was evaporated. The residue was crystallized from ethyl acetate, yielding 2.57 parts (61.6%) of 2-cyclopropyl-5-(1H-imidazol-1-ylmethyl)-1H-benzimidazole; mp. 184.3° C. (compound 168).

In a similar manner there were also prepared:

5-(1H-imidazol-1-ylmethyl)-2-(3-pyridinyl)-1H-benzimidazole; mp. 212.9° C. (compound 191);
5-(1H-imidazol-1-ylmethyl)-2-(3-pyridinyl)-1-(3-pyridinylmethyl)-1H-benzimidazole; mp. 179.7° C. (compound 192);
5-[(1H-imidazol-1-yl)(2-thienyl)methyl]-2-(3-pyridinyl)-1H-benzimidazole; mp. 135.4° C. (compound 193);
5-[(4-fluorophenyl)(1H-imidazol-1-yl)methyl]-2-(3-pyridinyl)-1H-benzimidazole; mp. 237.6° C. (compound 194);
5-[(1H-imidazol-1-yl)(3-pyridinyl)methyl]-2-(3-pyridinyl)-1H-benzimidazole; mp. 216.1° C. (compound 195);
5-[(3-chlorophenyl)(1H-imidazol-1-yl)methyl]-2-(3-

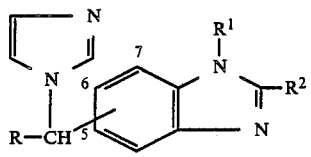

| No. | R | R¹ | R² | salt/base | position | mp (°C.) |
|---|---|---|---|---|---|---|
| 169 | H | H | i-$C_3H_7$ | base | 5 | 166.6 |
| 170 | 4-$CH_3O$—$C_6H_4$ | H | $CH_3$ | base | 5 | 121.9 |
| 171 | H | 3-pyridinyl methyl | $C_6H_5$ | base | 5 | 213.2 |
| 172 | $C_6H_5$ | H | $C_6H_5$ | base | 5 | 134.5 |
| 173 | $C_6H_5$ | H | 4-$CH_3$—$C_6H_4$ | 2HCl.1½$H_2O$ | 5 | 205.4 |
| 174 | $C_6H_5$ | H | 4-F—$C_6H_4$ | 2HCl.$H_2O$ | 5 | 194.6 |
| 175 | H | H | 4-$OCH_3$—$C_6H_4$ | 2HCl.$H_2$2HCl.$H_2O_{70.5}$ | | |
| 176 | $C_6H_5$ | H | 2-furanyl | 2HCl.$H_2O$ | 5 | 211.1 |
| 177 | H | H | (1H—imidazol-1-ylmethyl) | 3HCl | 5 | 253.5 |
| 178 | $C_6H_5$ | H | 3-$CF_3$—$C_6H_5$ | base | 5 | 181.6 |
| 179 | $C_6H_5$ | $CH_3$ | $C_6H_5$ | base | 5 | 164.4 |
| 180 | $CH_3$ | $CH_3$ | $CH_3$ | base | 5 | 163.4 |
| 181 | $C_2H_5$ | H | $CH_3$ | 2HCl | 5 | 235.3 |
| 182 | i-$C_3H_7$ | H | $CH_3$ | 2HCl.$H_2O$ | 5 | 214.8 |
| 183 | H | c-$C_6H_{11}$—$CH_2$ | $CH_3$ | base | 6 | 138.8 |
| 184 | H | c-$C_6H_{11}$—$CH_2$ | $C_6H_5$ | base | 6 | 141.8 |
| 185 | H | $C_6H_5$—$CH_2$ | $C_6H_5$ | base | 6 | 130.6 |
| 186 | H | $C_6H_5$—$CH_2$ | $CH_3$ | base | 6 | 105.3 |
| 187 | 3-Cl—$C_6H_4$ | H | H | 2$HNO_3$ | 5 | 205.9 |

In a similar manner there is also prepared:
6-(1H-imidazol-1-ylmethyl)-1,2-diphenyl-1H-benzimidazole (compound 188).

Example 31

A mixture of 5.05 parts of 4-[1-(1H-imidazol-1-yl)ethyl]-1,2-benzenediamine, 6.45 parts of ethyl 3-pyridinecarboximidate dihydrochloride, 4.27 parts of sodium acetate and 80 parts of absolute ethanol was stirred first for 16 hours at room temperature and for 1 hour at reflux. The reaction mixture was evaporated. There were added successively 50 parts of water and ammonium hydroxide. The product was filtered off, washed with water and 2-propanol and crystallized from ethanol. The product was filtered off and dried, yielding 5.1 parts (70%) of 5-[1-(1H-imidazol-1-yl)ethyl]-2-(3-pyridinyl)-1H-benzimidazole; mp. 253.7° C. (compound 189).

In a similar manner there were also prepared:
5-(1H-imidazol-1-yl)phenylmethyl]-2-(3-pyridinyl)-1H-benzimidazole; mp. 133.1° C. (compound 190);

pyridinyl)-1H-benzimidazole; mp. 232.0° C. (compound 196);
5-[bis(1H-imidazol-1-yl)methyl]-2-(3-pyridinyl)-1H-benzimidazole; mp. 271.0° C. (compound 197);
5-[1-(1H-imidazol-1-yl)ethyl]-2-(4-pyridinyl)-1H-benzimidazole; mp. 205.6° C. (compound 198);
(E)-2-[2-(2-furanyl)ethenyl]-5-[(1H-imidazol-1-yl)phenylmethyl]-1H-benzimidazole; mp. 134.7° C. (compound 199); and
(E)-5-[(1H-imidazol-1-yl)phenylmethyl]-2-(2-phenylethenyl)-1H-benzmidazole; mp. 140.6° C. (compound 200).

Example 32

To a stirred and cooled solution of 5.3 parts of 4-[(1H-imidazol-1-yl)phenylmethyl]-1,2-benzenediamine in 50 parts of acetic acid were added 3.3 parts of methyl 2-pyridinecarboximidate while still cooling. The whole was stirred for 8 hours at room temperature and then allowed to stand over weekend. The reaction mixture was evaporated. The residue was taken up in water and treated with activated charcoal. The whole was filtered and the filtrate was made alkaline with ammonium hydroxide. The product was filtered off and purified by column chromatography over silica gel using a mixture of trichloromethane and methanol (90:10 by volume) as eluent. The pure fractions were collected and the eluent was evaporated. The residue was dried in vacuo for 24 hours at 50° C., yielding 2.8 parts (40%) of 5-[(1H-imidazol-1-yl)phenylmethyl]-2-(2-pyridinyl)-1H-benzimidazole; mp. 123.3° C. (compound 201).

Example 33

A mixture of 2.75 parts of N²-(cyclohexylmethyl)-4-(1H-imidazol-1-ylmethyl)-1,2-benzenediamine, 1.85 parts of methyl 2,2,2-trifluoroethanimidate, 40 parts of methanol and 2.3 parts of trifluoroacetic acid was stirred for 7 hours at room temperature. The reaction mixture was made alkaline with methanol, saturated with ammonia. The solvent was evaporated in vacuo and the residue was purified by column chromatography over silica gel using a mixture of trichloromethane and methanol (95:5 by volume) as eluent. The pure fractions were collected and the eluent was evaporated in vacuo. The residue was dissolved in 11 parts of 2,2'-oxybispropane. The crystallized product was filtered off and dried, yielding 1.9 parts (52.4%) of 1-(cyclohexylmethyl)-6-(1H-imidazol-1-ylmethyl)-2-(trifluoromethyl)-1H-benzimidazole; mp. 165.4° C. (compound 202).

In a similar manner there were also prepared:
5-[(1H-imidazol-1-yl)(3-pyridinyl)methyl]-2-(trifluoromethyl)-1H-benzimidazole; mp. 124.9°–131.5° C. (compound 203); and
6-(1H-imidazol-1-ylmethyl)-1-(phenylmethyl)-2-(trifluoromethyl)-1H-benzimidazole; mp. 120.7° C. (compound 204).

Example 34

A mixture of 5 parts of 4-(1H-imidazol-1-ylmethyl)-1,2-benzenediamine, 3 parts of 3-thiophenecarboxaldehyde and 50 parts of a hydrochloric acid solution 3N was stirred for 36 hours at reflux temperature. After cooling, the mixture was poured into 100 parts of crushed ice and ammonium hydroxide. The product was extracted three times with 75 parts of trichloromethane. The combined extracts were dried, filtered and evaporated. The residue was purified by column chromatography (HPLC) over silica gel using a mixture of trichloromethane, methanol and ammonium hydroxide (90:10:0.1 by volume) as eluent. The pure fractions were collected and the eluent was evaporated. The residue was converted into the hydrochloride salt in 8 parts of 2-propanone and ethanol at 0° C. The salt was filtered off and crystallized from a mixture of methanol and 2-propanone. The product was filtered off and dried, yielding 0.8 parts (8.5%) of 5-(1H-imidazol-1-ylmethyl)-2-(3-thienyl)-1H-benzimidazole dihydrochloride; mp. >300° C. (dec.) (compound 205).

Example 35

A mixture of 7.4 parts of N-[2-amino-4-[1-(1H-imidazol-1-yl)ethyl]phenyl]acetamide, 10 parts of acetic acid and 100 parts of a hydrochloric acid solution 4N was stirred and refluxed for 3.5 hours. The reaction mixture was evaporated. The residue was dissolved in 20 parts of 2-propanol. The product was crystallized at room temperature. The product was filtered off and dried, yielding 8.1 parts (90.2%) of 5-[1-(1H-imidazol-1-yl)ethyl]-2-methyl-1H-benzimidazole dihydrochloride; mp. 236.2° C. (compound 206).

In a similar manner there were also prepared:
5-(1H-imidazol-1-ylmethyl)-2-methyl-1H-benzimidazole dihydrochloride; mp. 257.4° C. (compound 207); and
5-[1-(1H-imidazol-1-yl)ethyl]-1H-benzimidazole dihydrochloride; mp. 224.5° C. (compound 208).

Example 36

A mixture of 13.2 parts of 1-[(4-fluoro-3-nitrophenyl)methyl]-1H-imidazole, 13 parts of 4-pyridinemethanamine and 80 parts of ethanol was stirred for 6 hours at 60° C. 14.5 Parts of sodium hydroxide were added and the whole was stirred for 30 minutes at 60° C. The reaction mixture was evaporated. The residue was dissolved in 100 parts of water. Hydrochloric acid was added dropwise till a pH between 6 and 7 was reached. The product was filtered off, washed with water and 2-propanol and crystallized from 80 parts of 2-propanol. The product was filtered off and dried, yielding 10.7 parts (61%) of 6-(1H-imidazol-1-ylmethyl)-2-(4-pyridinyl)-1H-benzimidazol-1-ol; mp. 198.1° C. (compound 209).

Example 37

To a stirred mixture of 5.1 parts of 4-fluoro-N-[4-(1H-imidazol-1-yl-methyl)-2-nitrophenyl]benzenemethanamine and 80 parts of methanol were added 3.6 parts of sodium hydroxide and stirring was continued first for 10 minutes at room temperature and then for 20 hours at reflux temperature. After cooling, the reaction mixture was neutralized with a hydrochloric acid solution 2N. The precipitated product was filtered off, washed successively with water, methylbenzene and 2,2'-oxybispropane and dried, yielding 4.2 parts (91%) of 2-(4-fluorophenyl)-6-(1H-imidazol-1-ylmethyl)-1H-benzimidazol-1-ol; mp. 82° C. (compound 210).

In a similar manner there were also prepared:
6-(1H-imidazol-1-ylmethyl)-2-phenyl-1H-benzimidazol-1-ol monohydrate; mp. 136.8° C. (compound 211);
6-(1H-imidazol-1-ylmethyl)-2-(3-pyridinyl)-1H-benzimidazol-1-ol; mp. 207.5° C. (compound 212);
2-(4-fluorophenyl)-6-[(1H-imidazol-1-yl)phenylmethyl]-1H-benzimidazol-1-ol; mp. 150° C. (compound 213);
6-[1-(1H-imidazol-1-yl)ethyl]-2-phenyl-1H-benzimidazol-1-ol ethanedioate(2:3); mp. 179.6° C. (compound 214);
2-(4-fluorophenyl)-6-[1-(1H-imidazol-1-yl)ethyl]-1H-benzimidazol-1-ol as a residue (compound 215);
2-(4-fluorophenyl)-6-[1-(1H-imidazol-1-yl)-2-methylpropyl]-1H-benzimidazol-1-ol; mp. 271.2° C. (compound 216);
6-[1-(1H-imidazol-1-yl)-2-methylpropyl]-2-phenyl-1H-benzimidazol-1-ol; mp. 208.2° C. (compound 217); and
5-(1H-imidazol-1-ylmethyl)-2-phenyl-1H-benzimidazol-1-ol; mp. 203.1° C. (compound 218).

Example 38

A mixture of 4.9 parts of N-[4-[(1H-imidazol-1-yl)phenylmethyl]-2-nitrophenyl]acetamide, 12 parts of 2-propanol, saturated with hydrogen chloride and 200 parts of methanol was hydrogenated at normal pressure and at room temperature with 2 parts of platinium-on-charcoal catalyst 5%. After the calculated amount of hydrogen was taken up, the catalyst was filtered off and the filtrate was evaporated. The residue was dissolved in dichloromethane and water and then the solution was neutralized with an ammonium hydroxide solution. The dichloromethane layer was separated, dried, filtered and evaporated. The residue was purified by column chromatography over silica gel using a mixture of trichloromethane and methanol (85:15 by volume) as eluent. The pure fractions were collected and the eluent was evaporated, yielding 2.2 parts (40.6%) of 6-[(1H-imidazol-1-yl)phenylmethyl]-2-methyl-1H-benzimidazol-1-ol as a residue (compound 219).

In a similar manner there were also prepared:
6-(1H-imidazol-1-ylmethyl)-2-methyl-1H-benzimidazol-1-ol; mp. 224.9° C. (compound 220); and
5-(1H-imidazol-1-ylmethyl)-2-methyl-1H-benzimidazol-1-ol dihydrochloride (compound 221).

Example 39

A mixture of 4.04 parts of 4-(1H-imidazol-1-ylmethyl)-N¹-methyl-1,2-benzenediamine, 3.6 parts of 1,1'-carbonylbis[1H-imidazole] and 80 parts of tetrahydrofuran was stirred for about 100 hours at room temperature. The formed precipitate was filtered off, washed with tetrahydrofuran, dried and purified twice by column chromatography over silica gel using each time a mixture of trichloromethane, methanol and methanol, saturated with ammonia (90:5:5 by volume) as eluent. The pure fractions were collected and the eluent was evaporated. The solid residue was crystallized from 2-propanol. The product was filtered off, washed with 2-propanol and 2,2'-oxybispropane, and dried, yielding 3.5 parts (77%) of 5-(1H-imidazol-1-ylmethyl)-1-methyl-1H-benzimidazol-2-ol; mp. 207.2° C. (compound 222).

In a similar manner there were also prepared:
1,3-dihydro-5-[(1H-imidazol-1-yl)phenylmethyl]-2H-benzimidazol-2-one; mp. 162.1° C. (compound 223); and
5-[(3-chlorophenyl)(1H-imidazol-1-yl)methyl]-1,3-dihydro-2H-benzimidazol-2-one; mp. 172.0° C. (compound 224).

Example 40

A mixture of 5.28 parts of 4-[(1H-imidazol-1-yl)phenylmethyl]-1,2-benzenediamine, 2.3 parts of carbon disulfide, 80 parts of ethanol, 1.68 parts of potassium hydroxide and 11 parts of water was stirred for 3 hours at reflux temperature. After evaporation, 100 parts of water were added to the residue and the mixture was neutralized with 1.8 parts of a 0.03M acetic acid solution. After stirring, the precipitated product was filtered off, washed with 2-propanone and dried, yielding 4.3 parts (70.1%) of 5-[(1H-imidazol-1-yl)phenylmethyl]-1H-benzimidazole-2-thiol; mp. 260.1° C. (compound 225).

Example 41

A mixture of 4.5 parts of 5-(1H-imidazol-1-ylmethyl)-1-methyl-1H-benzimidazol-2-ol, 0.46 parts of a sodium hydride dispersion 50% and 56 parts of N,N-dimethylformamide was stirred for 30 minutes at 50° C. After the addition of 2.53 parts of (chloromethyl)benzene, the solution was stirred for 2 hours at 50° C. The N,N-dimethylformamide layer was evaporated in vacuo. The residue was diluted with water and the product was extracted with dichloromethane. The extract was dried, filtered and evaporated. The residue was crystallized from a mixture of 27 parts of ethyl acetate and 44 parts of 2,2'-oxybispropane. The product was filtered off and dried, yielding 5 parts (78.5%) of 1,3-dihydro-5-(1H-imidazol-1-ylmethyl)-1-methyl-3-(phenylmethyl)-2H-benzimidazol-2-one; mp. 129.4° C. (compound 226).

Example 42

To a stirred sodium methoxide solution previously prepared starting from 0.46 parts of sodium and 32 parts of methanol were added 6.16 parts of 6-(1H-imidazol-1-ylmethyl)-2-phenyl-1H-benzimidazol-1-ol. After stirring for a while, the whole was concentrated and 2 portions of 18 parts of methylbenzene were added. After evaporation, there were added successively 27 parts of N,N-dimethylformamide and a solution of 2.84 parts of iodomethane in 9 parts of N,N-dimethylformamide. The whole was stirred first for 10 minutes at room temperature and then for 30 minutes at 60° C. The reaction mixture was evaporated and 50 parts of water were added to the residue. The precipitated product was filtered off, washed with water and purified by filtration over silica gel using a mixture of trichloromethane and methanol (92.5:7.5 by volume) as eluent. The pure fractions were collected and the eluent was evaporated. The residue was crystallized from 2,2'-oxybispropane. The product was filtered off and dried, yielding 5.4 parts (88.7%) of 6-(1H-imidazol-1-ylmethyl)-1-methoxy-2-phenyl-1H-benzimidazole; mp. 142.1° C. (compound 227).

In a similar manner there were also prepared:

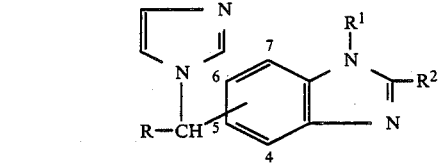

| No. | R | R¹ | R² | salt/base | position | mp (°C.) |
|---|---|---|---|---|---|---|
| 228 | H | CH₃O | CH₃ | 3H₂O | 6 | 84.2 |
| 229 | H | CH₃O | 3-pyridinyl | base | 6 | 114.2 |
| 230 | H | CH₃O | 4-pyridinyl | base | 6 | 127.8 |
| 231 | C₆H₅ | CH₃O | CH₃ | base | 6 | 117.6 |
| 232 | C₆H₅ | CH₃O | 4-F—C₆H₄ | base | 6 | 122.9 |
| 233 | C₆H₅ | i-C₃H₇O | 4-F—C₆H₄ | base | 6 | 146.6 |
| 234 | H | C₂H₅O | 4-F—C₆H₄ | base | 6 | 88.4 |
| 235 | CH₃ | CH₃O | 4-F—C₆H₄ | H₂O | 6 | 90.3 |
| 236 | H | CH₃O | CH₃ | base | 5 | 92.3 |
| 237 | H | CH₃O | 4-F—C₆H₄ | base | 6 | 114.5 |
| 238 | i-C₃H₇ | CH₃O | C₆H₅ | base | 6 | 179.4 |
| 239 | i-C₃H₇ | CH₃O | 4-F—C₆H₄ | base | 6 | 166.4 |
| 240 | CH₃ | CH₃O | C₆H₅ | base | 6 | 79.4 |

Example 43

A mixture of 2.7 parts of 2-(4-fluorophenyl)-6-[(1H-imidazol-1-yl)-phenylmethyl]-1H-benzimidazol-1-ol, 7 parts of a sodium hydroxide solution in water 1N and 20 parts of methanol was stirred for 15 minutes at room temperature. After evaporation, the residue was taken up in methylbenzene and the solvent was evaporated (this proces was repeated twice). The residue was dissolved in 22.5 parts of N,N-dimethylformamide and a solution of 0.89 parts of (chloromethyl)benzene in a small amount of N,N-dimethylformamide was added dropwise. Upon complete addition, stirring was continued for 1 hour at room temperature. After standing overnight at room temperature, the solvent was evaporated. Water was added to the residue and the product was extracted with dichloromethane. The extract was dried, filtered and concentrated. The concentrate was purified by column chromatography over silica gel using a mixture of trichloromethane and methanol (95:5 by volume) as eluent. The pure fractions were collected and the eluent was evaporated. The residue was crystallized from 17.5 parts of 2-propanol. The product was filtered off, washed with 2,2'-oxybispropane and 2-propanol and dried, yielding 2.1 parts (63.5%) of 2-(4-fluorophenyl)-6-[(1H-imidazol-1-yl)phenylmethyl]-1-phenylmethoxy)-1H-benzimidazole; mp. 177.6° C. (compound 241).

In a similar manner there were also prepared:

2-(4-fluorophenyl)-6-[(1H-imidazol-1-yl)phenylmethyl]-1-(2-propynyloxy)-1H-benzimidazole; mp. 152.4° C. (compound 242);

2-(4-fluorophenyl)-6-[(1H-imidazol-1-yl)phenylmethyl]-1-(2-propenyloxy)-1H-benzimidazole; mp. 109.8° C. (compound 243);

2-(4-fluorophenyl)-6-(1H-imidazol-1-ylmethyl)-1-(phenylmethoxy)-1H-benzimidazole; mp. 130.9° C. (compound 244); and 2-(4-fluorophenyl)-6-(1H-imidazol-1-ylmethyl)-1-(2-propenyloxy)-1H-benzimidazole; mp. 97.2° C. (compound 245).

In a similar manner there are also prepared:

6-(1H-imidazol-1-ylmethyl)-2-phenyl-1-(2-thienylmethoxy)-1H-benzimidazole (compound 246);

6-(1H-imidazol-1-ylmethyl)-2-phenyl-1-(3-pyridinylmethoxy)-1H-benzimidazole (compound 247);

1-(cyclohexylmethoxy)-6-(1H-imidazol-1-ylmethyl)-2-phenyl-1H-benzimidazole (compound 248);

6-(1H-imidazol-1-ylmethyl)-2-phenyl-1-(3-phenyl-2-propenyloxy)-1H-benzimidazole (compound 249);

6-(1H-imidazol-1-ylmethyl)-2-phenyl-1-(2-propynyloxy)-1H-benzimidazole (compound 250); and 6-(1H-imidazol-1-ylmethyl)-2-phenyl-1-(2-pyrimidinyloxy)-1H-benzimidazole (compound 251).

Example 44

A mixture of 2.7 parts of 6-[1-(1H-imidazol-1-yl)ethyl]-2-phenyl-1H-benzimidazol-1-ol, 0.2 parts of a sodium hydride dispersion 50% and 56 parts of N,N-dimethylformamide was stirred for 30 minutes at 60° C. After the addition of 0.5 parts of 2-(2-methoxyethoxy)-N,N-bis[2-(2-methoxyethoxy)ethyl]ethanamine and 1.11 parts of (chloromethyl)benzene, the whole was stirred for 3 hours at 50° C. The N,N-dimetnhylformamide layer was evaporated. The residue was dissolved in a hydrochloric acid solution 1N. The whole was washed with methylbenzene and treated with an ammonium hydroxide solution. The product was extracted with methylbenzene. The extract was dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was converted into the nitrate salt in 64 parts of ethyl acetate. The salt was filtered off and dried in vacuo, yielding 3.3 parts (72.0%) of 6-[1-(1H-imidazol-1-yl)ethyl]-2-phenyl-1-(phenylmethoxy)-1H-benzimidazole dinitrate; mp. 180.6° C. (compound 252).

Example 45

A mixture of 3 parts of 5-(1H-imidazol-1-ylmethyl)-2-phenyl-1H-benzimidazol-1-ol and 47 parts of N,N-dimethylformamide was stirred till a clear solution was obtained. 0.5 Parts of a sodium hydride dispersion 50% were added portionwise and stirring was continued till hydrogen evolution had ceased. Upon complete addition, 1.2 parts of (chloromethyl)benzene were added at once at room temperature. Upon complete reaction, the N,N-dimethylformamide layer was evaporated. The residue was taken up in water and the product was extracted with methylbenzene and a mixture of trichloromethane and methanol (90:10 by volume). The combined extracts were dried, filtered and evaporated. The residue was purified by column chromatography over silica gel using a mixture of trichloromethane and methanol (95:5 by volume) as eluent. The pure fractions were collected and the eluent was evaporated. The residue was crystallized from ethyl acetate. The product was filtered off, washed with a small amount of ethyl acetate and 2,2'-oxybispropane and dried in vacuo at 50° C., yielding 2.64 parts (66.7%) of 5-(1H-imidazol-1-ylmethyl)-2-phenyl-1-(phenylmethoxy)-1H-benzimidazole; (compound 253).

In a similar manner there were also prepared:

1-ethoxy-5-(1H-imidazol-1-ylmethyl)-2-phenyl-1H-benzimidazole; mp. 112.9° C. (compound 254); and 5-(1H-imidazol-1-ylmethyl)-1-methoxy-2-phenyl-1H-benzimidazole; mp. 106.7° C. (compound 255).

Example 46

During 6 days gaseous hydrogen chloride was bubbled through a mixture of 14.5 parts of 1,3-dihydro-5-[(1H-imidazol-1-yl)methyl]-2H-benzimidazol-2-one and 255 parts of phosphoryl chloride at 90° C. The resulting solution was evaporated and 300 parts of ice water were added to the residue. An ammonium hydroxide solution was added dropwise till alkaline, whereupon the product was precipitated. The latter was filtered off (the filtrate was set aside) washed with water and dried in vacuo, yielding a first fraction of 14.1 parts of 2-chloro-5-(1H-imidazol-1-ylmethyl)-1H-benzimidazole (compound 256). The aqueous filtrate (see above) was salted out with potassium carbonate and extracted with dichloromethane. The organic extract was dried, filtered and evaporated. The residue was dried in vacuo, yielding a second fraction of 1.4 parts of 2-chloro-5-(1H-imidazol-1-yl-methyl)-1H-benzimidazole (compound 256). Total yield: 15.5 parts (98.4%) of 2-chloro-5-(1H-imidazol-1-ylmethyl)-1H-benzimidazole (compound 256).

In a similar manner there was also prepared:

2-chloro-5-(1H-imidazol-1-ylmethyl)-1-methyl-1H-benzimidazole as a residue (compound 257).

Example 47

A mixture of 4.4 parts of 1H-imidazole and 5 parts of 2-chloro-5-(1H-imidazol-1-ylmethyl)-1H-benzimidazole was molten together for 1 hour at 140° C. The sticky mixture was taken up in a mixture of ethanol and potassium carbonate. The supernatant liquid was decanted and evaporated to dry. The residue was purified by column chromatography over silica gel using a mixture of trichloromethane, methanol and ammonium hydroxide (90:10:0.1 by volume) as eluent. The pure fractions were collected and the eluent was evaporated. The residue was taken up in 15 parts of water. The product was filtered off and crystallized from a mixture of methanol and ethyl acetate, yielding 0.95 parts (17%) of 2-(1H-imidazol-1-yl)-5-(1H-imidazol-1-ylmethyl)-1H-benzimidazole; mp. 226.2° C. (compound 258).

Example 48

A mixture of 3 parts of ethyl 4-[5-(1H-imidazol-1-ylmethyl)-1H-benzimidazol-2-yl]benzoate and 50 parts of a hydrochloric acid solution 6N was stirred and refluxed for 12 hours. The reaction mixture was evaporated to dry. The residue was taken up in 2 parts of water and 2-propanone. The product was filtered off and dried, yielding 2 parts (59%) of 4-[5-(1H-imidazol-1-ylmethyl)-1H-benzimidazol-2-yl]benzoic acid dihydrochloride. monohydrate; mp. 288.2° C. (compound 259).

In a similar manner there was also prepared:
3-[5-(1H-imidazol-1-ylmethyl)-1H-benzimidazol-2-yl]benzoic acid dihydrochloride,hemihydrate; mp. 283.0° C. (compound 260).

Example 49

A mixture of 2.4 parts of ethyl 4-[5-[(1H-imidazol-1-yl)phenylmethyl]-1H-benzimidazol-2-yl]benzoate and 30 parts of a sodium hydroxide solution 3N was stirred for 12 hours at room temperature. The reaction mixture was poured into 50 parts of ice water and the whole was acidified with a sulfuric acid solution 3N to pH 5.5 The product was extracted with a mixture of trichloromethane and methanol. The extract was dried, filtered and evaporated. The residue was purified by column chromatography over silica gel using a mixture of trichloromethane and methanol (80:20 by volume) as eluent. The pure fractions were collected and the eluent was evaporated. The residue was converted into the hydrochloride salt in 2-propanol. The mixture was evaporated to dry and the residue was taken up in a mixture of 2-propanol, water and 2-propanone. The product was filtered off and dried, yielding 1.41 parts (49.1%) of 4-[5-[(1H-imidazol-1-yl)phenylmethyl]-1H-benzimidazol-2-yl]benzoic acid dihydrochloride,hydrate(2:5); mp. 225.5° C. (compound 261).

In a similar manner there were also prepared:
4-[5-[1-(1H-imidazol-1-yl)ethyl]-1H-benzimidazol-2-yl]benzoic acid dihydrochloride,monohydrate; mp. 260.8° C. (compound 262); and
4-[5-[1-(1H-imidazol-1-yl)ethyl]-1-methyl-1H-benzimidazol-2-yl]benzoic acid dihydrochloride,dihydrate; mp. 182.9° C. (compound 263).

Example 50

A mixture of 1.5 parts of 5-[(1H-imidazol-1-yl)phenylmethyl]-α-phenyl-1H-benzimidazole-2-methanol, 1.4 parts of potassium dichromate and 25 parts of acetic acid was stirred for 45 minutes at room temperature. Water was added to the mixture and the whole was made alkaline with concentrated ammonium hydroxide. The product was extracted with a mixture of trichloromethane and methanol (95:5 by volume). The extract was dried, filtered and evaporated. The residue was purified twice by column chromatography over silica gel using a mixture of trichloromethane, methanol and methanol, saturated with ammonia (90:5:5 by volume) as eluent. The pure fractions were collected and the eluent was evaporated. The residue was crystallized from 63 parts of ethyl acetate. The product was filtered off and dried in vacuo at 100° C. during 17 hours, yielding 0.8 parts (54%) of [5-[(1H-imidazol-1-yl)phenylmethyl]-1H-benzimidazol-2-yl] phenylmethanone; mp. 223.3° C. (compound 264).

Example 51

To a stirred and heated (60° C.) solution of 8 parts of 5-(1H-imidazol-1-ylmethyl)-1H-benzimidazole-2-methanol, 4.7 parts of potassium carbonate and 100 parts of water were added portionwise 11.1 parts of potassium permanganate. Upon completion, stirring was continued for 15 minutes at 60° C. The manganese(IV) oxide was filtered off over diatomaceous earth. After cooling, the filtrate was treated with glacial acetic acid to pH 5.5. The whole was evaporated to dry. The residue was taken up in a small amount of water. The product was filtered off and dried for 24 hours, yielding 3.1 parts (31.8%) of 5-(1H-imidazol-1-ylmethyl)-1H-benzimidazole-2-carboxylic acid dihydrate (compound 265).

In a similar manner there was also prepared:
5-[1-(1H-imidazol-1-yl)ethyl]-1H-benzimidazole-2-carboxylic acid as a residue (compound 266).

Example 52

A mixture of 2.3 parts of 5-(1H-imidazol-1-ylmethyl)-1H-benzimidazole-2-carboxylic acid and 80 parts of thionyl chloride was stirred for 3 hours at reflux temperature. The reaction mixture was evaporated to dry, yielding 4.3 parts of 3,9-bis(1H-imidazol-1-yl-methyl)-6H,13H-pyrazino[1,2-a:4,5-a']bisbenzimidazole6,13-dione which were poured into a solution of 3.8 parts of sodium methoxide in 40 parts of methanol. The whole was stirred for 1 hour at room temperature. The whole was neutralised with 10 parts of acetic acid and concentrated to dry. The concentrate was taken up in a sodium hydrogen carbonate solution 10% and the product was extracted with a mixture of dichloromethane and methanol (90:10 by volume). The combined extracts were dried, filtered and evaporated. The residue was purified by column chromatography over silica gel using a mixture of dichloromethane and methanol (90:10 by volume) as eluent. The pure fractions were collected and the eluent was evaporated. The residue was crystallized from 2-propanone. The product was filtered off and dried, yielding 0.7 parts (26.9%) of methyl 5-(1H-imidazol-1-ylmethyl)-1H-benzimidazole-2-carboxylate; mp. 228° C. (compound 267).

In a similar manner there was also prepared:
methyl 5-[1-(1H-imidazol-1-yl)ethyl]-H-benzimidazole-2-carboxylate; mp. 161.5° C. (compound 268).

Example 53

A solution of 0.7 parts of methyl 5-(1H-imidazole-1-ylmethyl)-1H-benzimidazole-2-carboxylate in 2.7 parts of a sodium hydroxide solution 1N was stirred for 3 hours at 20° C. After the addition of ethanol, the whole was evaporated to dry at <60° C. The residue was taken up in 2-propanone. The product was filtered off and dried for 1 hour at 80° C., yielding b 0.7 parts (94.8%) of sodium 5-(1H-imidazol-1-ylmethyl-1H-benzimidazole-2-carboxylate hemihydrate; mp. 253.3° C. (compound 269).

In a similar manner there was also prepared:
sodium 5-[1-(1H-imidazol-1-yl)ethyl]-1H-benzimidazole-2-carboxylate; mp. 245.6° C. (compound 270).

Example 54

A mixture of 3.2 parts of (+)-2-methyl-5-[[2-(methylthio)-1H-imidazol-1-yl]phenylmethyl]-1H-benzimidazole, 0.1 parts of Raney nickel catalyst and 200 parts of methanol was stirred for 3 hours at reflux temperature. The reaction mixture was filtered while hot over diatomaceous earth, washed with boiling ethanol and the filtrate was evaporated, yielding 1.5 parts (52.0%) of (+)-5-[-(1H-imidazol-1-yl)-phenylmethyl]-2-methyl-1H-benzimidazole as a residue (compound 271).

In a similar manner there was also prepared:
(−)-5[-(1H-imidazol-1-yl)phenylmethyl]-2-methyl-1H-benzimidazole as a residue (compound 272).

C. PHARMACOLOGICAL EXAMPLES

The useful androgenic hormone biosynthesis inhibitory properties of the compounds of formula (I) can be demonstrated in the following test procedures.

Example 55

PIG TESTIS MICROSOMES TEST

For example, one may analyze spectral changes in cytochrome P-450 (cyt. P-450) spectrum which are induced by interactions of compounds of formula (I) with the cyt. P-450 isozymes in isolated subcellular fractions such as, for example, piglet testes microsomes, adrenal cortex microsomes and bovine adrenal cortex mitochondria.

Piglet (≦21 days) testes were obtained by castration. The testes were decapsulated, minced in 0.15M KCl, washed and homogenized in 2 vol (of the original vol) of 0.25M sucrose containing b 20 mM KCl, 1 mM EDTA and 20 mM Tris-buffer (pH 7.4). The homogenate was centrifuged at 1500 g for 10 min and the cell-free supernatant at 10 000 g for 20 min. The pelleted mitochondrial fraction was removed and the microsomal membranes were collected by centrifugation at 105000 g for 60 min. The pellet containing the microsomal membranes was suspended in 0.1M potassium phosphate buffer (pH 7.4) and stored at −80° C. The cytochrome P-450 (cyt. P-450) content was determined by measuring the reduced carbon monoxide difference spectrum using 91 $cm^{-1}$ $mM^{-1}$ as extinction coefficient. The absorbance increment between 450 nm and 490 nm was used for the calculation of the cyt. P-450 content. The interaction(s) of the compounds of formula (I) with the cyt. P-450 isozymes in the isolated membrane fraction was examined by analyzing spectral changes of the cyt. P-450 induced by the compound. The membranal fractions were diluted in 0.1M potassium phosphate buffer, pH 7.4 to obtain a cyt. P-450 content of 0.1 nmole/ml. The suspension was divided between the reference and sample cuvettes. A base-line of equal light absorbance was established. Increasing concentrations of the compound of formula (I) dissolved in dimethyl sulfoxide (DMSO) were added to the sample cuvette while equal amounts of DMSO were added to the reference cuvette. The cyt. P-450 isozymes were reduced with a few grains of sodium dithionite. The cuvettes were bubbled for 30 sec with CO and then tightly closed. Upon addition of the reductant, dithionite, and saturation with CO the reduced cyt. P-450-CO complex shows a typical spectrum with an absorption peak at 450 nm. However, when the cyt. P-450 isozymes were contacted with a compound of formula (I), prior to reduction and saturation with CO only a small absorption peak at 450 nm was observed after bubbling with CO. The thus obtained difference spectrum was recorded 30 secondes after addition of the reductant.

The difference spectrum was recorded 30 sec after addition of the reductant. By a weighed non-linear regression procedure, a sigmoidal dose-response model was fitted to the individual observations and the corresponding $IC_{50}$-values (50% decrease in the peak height of the Soret band of the reduced CO-complex) was determined. Said $IC_{50}$-values of a number of compounds of formula (I) are depicted in column (a) of table (I).

Example 56

TESTOSTERONE IN VIVO TEST

Male rats were administered orally a test compound as a solution or as a suspension in aqueous medium. One four following drug or placebo administration, a luteinizing hormone releasing hormone-analogue was injected intramuscularly and an anaesthetic was administered intraperitonally. Two hours after the oral administration of the test compound the rats were decapitated, and the blood was collected on heparine. Plasma testosterone concentrations were measured by standard radio-immunological procedures. A 50% inhibition relative to the placebo values was considered as the criterion of testosterone inhibitory activity. $ED_{50}$-values were determined by probit analysis. Said $ED_{50}$-values of a number of compounds of formula (I) are depicted in column (b) of table (I). The results in this table are not given for the purpose of limiting the invention thereto but only to exemplify the useful pharmacological properties of all the compounds within the scope of formula (I)

TABLE I

| Compound No. | cyt. P-450 $IC_{50}$-values in μM | testosterone in vivo $ED_{50}$-values in mg/kg |
|---|---|---|
| 227 | 0.3 | 2.5 |
| 206 | 0.5 | <2.5 |
| 111 | 0.3 | <10 |
| 112 | 0.5 | 2.5 |
| 222 | 1.1 | <2.5 |
| 113 | 0.1 | <10 |
| 125 | 0.2 | 2.5 |
| 95 | 0.2 | — |
| 127 | 0.1 | 10 |
| 97 | 0.2 | — |
| 93 | 0.2 | 2.5 |
| 122 | 0.1 | 2.5 |
| 99 | 0.1 | — |
| 130 | 0.2 | — |
| 101 | 0.1 | — |
| 190 | 0.1 | 10 |
| 229 | 0.4 | 2.5 |
| 194 | 0.4 | — |
| 196 | 0.2 | — |
| 133 | 0.3 | <2.5 |
| 136 | 0.4 | <2.5 |
| 173 | 0.2 | <2.5 |
| 189 | 1 | 2.5 |
| 141 | 0.9 | 2.5 |
| 142 | 0.3 | 2.5 |
| 174 | 0.2 | <2.5 |
| 147 | 0.2 | — |
| 49 | 0.5 | <2.5 |
| 92 | 0.3 | <2.5 |
| 51 | — | 2.5 |
| 71 | — | 2.5 |
| 53 | 0.6 | 2.5 |
| 75 | 0.2 | — |
| 115 | 0.2 | 2.5 |
| 83 | 0.3 | <2.5 |
| 231 | 0.1 | 2.5 |
| 54 | 0.2 | 2.5 |

TABLE I-continued

| Compound No. | cyt. P-450 IC$_{50}$-values in μM | testosterone in vivo ED$_{50}$-values in mg/kg |
|---|---|---|
| 56 | 0.11 | — |
| 28 | 0.55 | 2.5 |
| 39 | 0.11 | — |
| 179 | 0.14 | — |
| 55 | 0.077 | — |
| 29 | 0.19 | — |
| 60 | 0.095 | — |
| 84 | 0.19 | <2.5 |
| 85 | 0.085 | — |
| 119 | 0.21 | 2.5 |
| 30 | 0.13 | 2.5 |
| 235 | 0.073 | 2.5 |
| 182 | 0.48 | 2.5 |
| 160 | 0.384 | 2.5 |
| 34 | 0.17 | 2.5 |
| 78 | 0.32 | <2.5 |
| 264 | 0.13 | — |
| 155 | 0.11 | — |
| 36 | 0.15 | — |
| 102 | 0.43 | <2.5 |

(D) Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

Example 57

ORAL DROPS 500 g of the A.I. was dissolved in 0.5 l of 2-hydroxypropanoic acid and 1.5 l of the polyethylene glycol at 60°~80° C. After cooling to 30°~40° C. there were added 35 l of polyethylene glycol and the mixture was stirred well. Then there was added a solution of 1750 g of sodium saccharin in 2.5 l of purified water and while stirring there were added 2.5 l of cocoa flavor and polyethylene glycol q.s. to a volume of 50 l, providing an oral drop solution comprising 10 mg of the A.I. per ml. The resulting solution was filled into suitable containers.

Example 58

ORAL SOLUTION 9 g of methyl 4-hydroxybenzoate and 1 g of propyl 4-hydroxybenzoate were dissolved in 4 l of boiling purified water. In 3 l of this solution were dissolved first 10 g of 2,3-dihydroxybutanedioic acid and thereafter 20 g of the A.I. The latter solution was combined with the remaining part of the former solution and 12 l 1,2,3-propanetriol and 3 l of sorbitol 70% solution were added thereto. 40 g of sodium saccharin were dissolved in 0.5 l of water and 2 ml of raspberry and 2 ml of gooseberry essence were added. The latter solution was combined with the former, water was added q.s. to a volume of 20 l providing an oral solution comprising 20 mg of the active ingredient per teaspoonful (5 ml). The resulting solution was filled in suitable containers.

Example 59

CAPSULES 20 g of the A.I., 6 g sodium lauryl sulfate, 56 g starch, 56 g lactose, 0.8 g colloidal silicon dioxide, and 1.2 g magnesium stearate were vigorously stirred together. The resulting mixture was subsequently filled into 1000 suitable hardened gelating capsules, comprising each 20 mg of the active ingredient.

Example 60

FILM-COATED TABLETS

Preparation of tablet core

A mixture of 100 g of the A.I., 570 g lactose and 200 g starch was mixed well and thereafter humidified with a solution of 5 g sodium dodecyl sulfate and 10 g polyvinylpyrrolidone (Kollidon-K 90 ®) in about 200 ml of water. The wet powder mixture was sieved, dried and sieved again. Then there was added 100 g microcrystalline cellulose (Avicel ®) and 15 g hydrogenated vegetable oil (Sterotex ®). The whole was mixed well and compressed into tablets, giving 10.000 tablets, each containing 10 mg of the active ingredient.

Coating

To a solution of 10 g methyl cellulose (Methocel b 60 HG ®) in b 75 ml of denaturated ethanol there was added a solution of 5 g of ethyl cellulose (Ethocel 22 cps ®) in 150 ml of dichloromethane. Then there were added 75 ml of dichloromethane and 2.5 ml 1,2,3-propane-triol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated colour suspension (Opaspray K-1-2109 ®) and the whole was homogenated. The tablet cores were coated with the thus obtained mixture in a coating apparatus.

Example 61

INJECTABLE SOLUTION 1.8 g methyl 4-hydroxybenzoate and 0.2 g propyl 4-hydroxybenzoate were dissolved in about 0.5 l of boiling water for injection. Aftercooling to about 50° C. there were added while stirring 4 g lactic acid, 0.05 g propylene glycol and 4 g of the A.I. . The solution was cooled to room temperature and supplemented with water for injection q.s. ad 1 l volume, giving a solution of 4 mg A.I. per ml. The solution was sterilized by filtration (U.S.P. XVII p. 811) and filled in sterile containers.

Example 62

SUPPOSITORIES 3 g A.I. was dissolved in a solution of 3 g 2,3-dihydroxybutanedioic acid in 25 ml polyethylene glycol 400. 12 g Surfactant (SPAN ®) and triglycerides (Witepsol 555 ®) q.s. ad 300 g were molten together. The latter mixture was mixed well with the former solution. The thus obtained mixture was poured into moulds at a temperature of 37°~38° C. to form 100 suppositories each containing 30 mg of the active ingredient.

What is claimed is:

1. A chemical compound having the formula

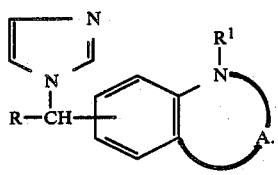

(I)

or pharmaceutically acceptable acid addition, metal or amine substitution salt or a stereochemically isomeric form thereof, wherein R is hydrogen; $C_{1-10}$alkyl; $C_{3-7}$cycloalkyl; $Ar^1$ or $Ar^1$-$C_{1-6}$alkyl;

$R^1$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;

A is a bivalent radical having the formula $-CR^2=N-$ or (a)

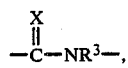 (b)

wherein the carbon atom in the bivalent radical (a) or (b) is connected to $-NR^1$;

said $R^2$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl or hydroxy; $C_{1-10}$alkyloxy; $C_{1-6}$alkyloxy substituted with $Ar^1$ or $C_{3-7}$cycloalkyl; $C_{3-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl or $Ar^1$-(CHOH)—;

said X being O or S;

said $R^3$ being hydrogen, $C_{1-6}$alkyl or $Ar^2$-$C_{1-6}$alkyl;

$Ar^1$ is phenyl, substituted phenyl, pyridinyl, aminopyridinyl, imidazolyl, thienyl, halothienyl, furanyl, halofuranyl or thiazolyl;

$Ar^2$ is phenyl or substituted phenyl;

in $Ar^1$ and $Ar^2$ said substituted phenyl being phenyl substituted with 1 or 2 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

2. A chemical compound according to claim 1 wherein A is a bivalent radical of formula (a); $R^1$ is hydrogen; $C_{3-7}$cycloalkyl; $Ar^2$; $C_{1-10}$alkyl; $C_{1-6}$alkyl substituted with $Ar^1$ or $C_{3-7}$cycloalkyl; hydroxy or $C_{1-6}$alkyloxy; and $R^2$ is hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$; quinolinyl or indolinyl; $C_{1-6}$alkyloxy; $C_{3-6}$alkenyl substituted with $Ar^1$; or $Ar^2$-carbonyl.

3. A chemical compound according to claim 2 wherein the 1H-imidazol-1-ylmethyl moiety is attached to the benzimidazole at either the 5 or 6 position of the benzimidazole ring; R is hydrogen; $C_{1-6}$alkyl or $Ar^1$; $R^1$ is hydrogen; $C_{1-6}$alkyl or $Ar^2$-$C_{1-6}$alkyl; and $R^2$ is hydrogen; di- or tri-halomethyl; $C_{1-6}$alkyl substituted with $Ar^1$, quinolinyl or indolinyl; $C_{1-10}$alkyl; $Ar^1$; $C_{1-6}$alkyloxy or $Ar^2$-carbonyl.

4. A chemical compound according to claim 3 wherein R is $C_{1-6}$alkyl or $Ar^2$; $R^1$ is hydrogen; and $R^2$ is hydrogen, $C_{1-6}$alkyl or $Ar^1$.

5. A chemical compound according to claim 1 wherein the compound is 5-[(3-chlorophenyl)(1H-imidazol-1-yl)methyl]-1H-benzimidazole.

6. A chemical compound according to claim 1 wherein the compound is 5-[(1H-imidazol-1-yl)phenylmethyl]-2-methyl-1H-benzimidazole.

7. A pharmaceutical composition for the treatment of androgen dependent disorders in mammals comprising an inert carrier and as active ingredient a pharmaceutically acceptable amount of a compound having the formula

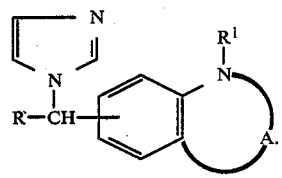

(I)

or pharmaceutically acceptable acid addition, metal or amine substitution salt or a stereochemically isomeric form thereof, wherein R is hydrogen; $C_{1-10}$alkyl; $C_{3-7}$cycloalkyl; $Ar^1$ or $Ar^1$-$C_{1-6}$alkyl;

$R^1$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;

A is a bivalent radical having the formula $-CR^2=N-$ or (a)

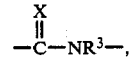 (b)

wherein the carbon atom in the bivalent radical (a) or (b) is connected to $-NR^1$;

said $R^2$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl or hydroxy; $C_{1-10}$alkyloxy; $C_{1-6}$alkyloxy substituted with $Ar^1$ or $C_{3-7}$cycloalkyl; $C_{3-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl or $Ar^1$-(CHOH)—;

said X being O or S;

said $R^3$ being hydrogen, $C_{1-6}$alkyl or $Ar^2$-$C_{1-6}$alkyl;

$Ar^1$ is phenyl, substituted phenyl, pyridinyl, aminopyridinyl, imidazolyl, thienyl, halothienyl, furanyl, halofuranyl or thiazolyl;

$Ar^2$ is phenyl or substituted phenyl;

in $Ar^1$ and $Ar^2$ said substituted phenyl being phenyl substituted with 1 or 2 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

8. A pharmaceutical composition according to claim 7 wherein A is a bivalent radical of formula (a); $R^1$ is hydrogen; $C_{3-7}$cycloalkyl; $Ar^2$; $C_{1-10}$alkyl; $C_{1-6}$alkyl substituted with $Ar^1$ or $C_{3-7}$cycloalkyl; hydroxy or $C_{1-}$ 6alkyloxy; and $R^2$ is hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, quinolinyl or indolinyl; $C_{1-6}$alkyloxy; $C_{3-6}$alkenyl substituted with $Ar^1$; or $Ar^2$-carbonyl.

9. A pharmaceutical composition according to claim 8 wherein the 1H-imidazol-1-ylmethyl moiety is substituted on either the 5 or 6 position of the benzimidazole ring; R is hydrogen; $C_{1-6}$alkyl or $Ar^1$; $R^1$ is hydrogen; $C_{1-6}$alkyl or $Ar^2$-$C_{1-6}$alkyl; and $R^2$ is hydrogen; di- or tri-halomethyl; $C_{1-6}$alkyl substituted with $Ar^1$, quinolinyl or indolinyl; $C_{1-10}$alkyl; $Ar^1$; $C_{1-6}$alkyloxy or $Ar^2$-carbonyl.

10. A pharmaceutical composition according to claim 9 wherein R is $C_{1-6}$alkyl or $Ar^2$; $R^1$ is hydrogen; and $R^2$ is hydrogen, $C_{1-6}$alkyl or $Ar^1$.

11. A pharmaceutical composition according to claim 7 wherein the compound is 5-[(3-chlorophenyl)(1H-imidazol-1-yl)methyl]-1H-benzimidazole.

12. A pharmaceutical composition according to claim 7 wherein the compound is 5-[(1H-imidazol-1-yl)phenylmethyl]-2-methyl-1H-benzimidazole.

13. A method of treating mammals suffering from androgen dependent disorders, said method comprising the systemic administration to said mammals of an amount effective to treat androgen dependent disorders of a compound having the formula

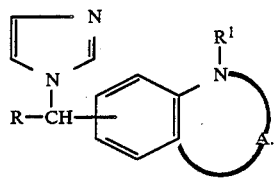

or pharmaceutically acceptable acid addition, metal or amine substitution salt or a stereochemically isomeric form thereof, wherein R is hydrogen; $C_{1-10}$alkyl; $C_{3-7}$cycloalkyl; $Ar^1$ or $Ar^1$-$C_{1-6}$alkyl;

$R^1$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyloxy substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;

A is a bivalent radical having the formula $$-CR^2=N- \quad \text{or} \quad (a)$$

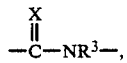

wherein the carbon atom in the bivalent radical (a) or (b) is connected to $-NR^1$;

said $R^2$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, $C_{3-7}$cycloalkyl, quinolinyl, indolinyl or hydroxy; $C_{1-10}$alkyloxy; $C_{1-6}$alkyloxy substituted with $Ar^1$ or $C_{3-7}$cycloalkyl; $C_{3-6}$alkenyl optionally substituted with $Ar^1$; $Ar^2$-oxy; $C_{1-6}$alkyloxycarbonyl; carboxyl; $C_{1-6}$alkylcarbonyl; $Ar^1$-carbonyl or $Ar^1$—(CHOH)—;

said X being O or S;

said $R^3$ being hydrogen, $C_{1-6}$alkyl or $Ar^2$-$C_{1-6}$alkyl;

$Ar^1$ is phenyl, substituted phenyl, pyridinyl, aminopyridinyl, imidazolyl, thienyl, halothienyl, furanyl, halofuranyl or thiazolyl;

$Ar^2$ is phenyl or substituted phenyl;

in $Ar^1$ and $Ar^2$ said substituted phenyl being phenyl substituted with 1 or 2 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

14. A method according to claim 13 wherein A is a bivalent radical of formula (a); $R^1$ is hydrogen; $C_{3-7}$cycloalkyl; $Ar^2$; $C_{1-10}$alkyl; $C_{1-6}$alkyl substituted with $Ar^1$ or $C_{3-7}$cycloalkyl; hydroxy or $C_{1-6}$alkyloxy; and $R^2$ is hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with $Ar^1$, quinolinyl or indolinyl; $C_{1-6}$alkyloxy; $C_{3-6}$alkenyl substituted with $Ar^1$; or $Ar^2$-carbonyl.

15. A method according to claim 14 wherein the 1H-imidazol-1-ylmethyl moiety is substituted on either the 5 or 6 position of the benzimidazole ring; R is hydrogen; $C_{1-6}$alkyl or $Ar^1$; $R^1$ is hydrogen; $C_{1-6}$alkyl or $Ar^2$-$C_{1-6}$alkyl; and $R^2$ is hydrogen; di- or tri-halomethyl; $C_{1-6}$alkyl substituted with $Ar^1$, quinolinyl or indolinyl; $C_{1-10}$alkyl; $Ar^1$; $C_{1-6}$alkyloxy or $Ar^2$-carbonyl.

16. A method according to claim 15 wherein R is $C_{1-6}$alkyl or $Ar^2$; $R^1$ is hydrogen; and $R^2$ is hydrogen, $C_{1-6}$alkyl or $Ar^1$.

17. A method according to claim 13 wherein the compound is 5-[(3-chlorophenyl)(1H-imidazol-1-yl)methyl]-1H-benzimidazole.

18. A method of inhibiting androgen synthesis in mammals, said method comprising the systemic administration to said mammals of an androgen synthesis inhibitory amount of a compound having the formula

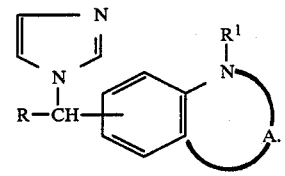

or pharmaceutically acceptable acid addition, metal or amine substitution salt or a stereochemically isomeric form thereof, wherein R is hydrogen; $C_{1-10}$alkyl; $C_{3-7}$cycloalkyl; $Ar^1$ or $Ar^1$-$C_{1-6}$alkyl;

$R^1$ is hydrogen; $C_{3-7}$cycloalkyl; $Ar^1$; $C_{1-10}$alkyl; $C_{1-6}$alkyl substituted with $Ar^1$ or $C_{3-7}$cycloalkyl; hydroxy; $C_{1-10}$alkyloxy; $C_{1-6}$alkyl substituted with $Ar^1$ or $C_{3-7}$cycloalkyl; $C_{3-6}$alkenyloxy optionally substituted with $Ar^2$; $C_{3-6}$alkynyloxy optionally substituted with $Ar^2$; or $Ar^1$-oxy;

A is a bivalent radical having the formula $$-CR^2=N- \quad \text{or} \quad (a)$$

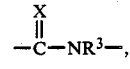

wherein the carbon atom in the bivalent radical (a) or (b) is connected to $-NR^1$;

said $R^2$ being hydrogen; halo; $C_{1-4}$alkyl substituted with up to 4 halo atoms; $C_{3-7}$cycloalkyl; $Ar^1$; quinolinyl; indolinyl; $C_{1-10}$alkyl; $C_{1-6}$alkyl substituted with Ar$^1$, C$_{3-7}$cycloalkyl, quinolinyl, indolinyl or hydroxy; C$_{1-10}$alkyloxy; C$_{1-6}$alkyloxy substituted with Ar$^1$ or C$_{3-7}$cycloalkyl; C$_{3-6}$alkenyl optionally substituted with Ar$^1$; Ar$^2$-oxy; C$_{1-6}$alkyloxycarbonyl; carboxyl; C$_{1-6}$alkylcarbonyl; Ar$^1$-carbonyl or Ar$^1$—(CHOH)—;

said X being O or S;

said R$^3$ being hydrogen, C$_{1-6}$alkyl or Ar$^2$-C$_{1-6}$alkyl;

Ar$^1$ is phenyl, substituted phenyl, pyridinyl, aminopyridinyl, imidazolyl, thienyl, halothienyl, furanyl, halofuranyl or thiazolyl;

Ar$^2$ is phenyl or substituted phenyl;

in Ar$^1$ and Ar$^2$ said substituted phenyl being phenyl substituted with 1 or 2 substituents each independently selected from halo, hydroxy, trifluoromethyl, C$_{1-6}$alkyl, C$_{1-6}$alkyloxy, cyano, amino, mono- and di(C$_{1-6}$alkyl)amino, nitro, carboxyl, formyl and C$_{1-6}$alkyloxycarbonyl.

19. A method of inhibiting the androgen formation from C$_{21}$ steroids in mammals, said method comprising the systemic administration to said mammals of an androgen synthesis inhibitory amount of a compound having the formula

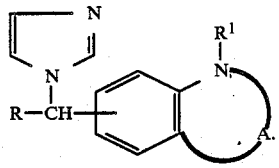

(I)

or pharmaceutically acceptable acid addition, metal or amine substitution salt or a stereochemically isomeric form thereof, wherein R is hydrogen; C$_{1-10}$alkyl; C$_{3-7}$cycloalkyl; Ar$^1$ or Ar$^1$-C$_{1-6}$alkyl;

R$^1$ is hydrogen; C$_{3-7}$cycloalkyl; Ar$^1$; C$_{1-1}$alkyl; C$_{1-6}$alkyl substituted with Ar$^1$ or C$_{3-7}$cycloalkyl; hydroxy; C$_{1-10}$alkyloxy; C$_{1-6}$alkyloxy substituted with Ar$^1$ or C$_{3-7}$cycloalkyl; C$_{3-6}$alkenyloxy optionally substituted with Ar$^2$; C$_{3-6}$alkynyloxy optionally substituted with Ar$^2$; or Ar$^1$-oxy;

A is a bivalent radical having the formula

wherein the carbon atom in the bivalent radical (a) or (b) is connected to —NR$^1$;

said R$^2$ being hydrogen; halo; C$_{1-4}$alkyl substituted with up to 4 halo atoms; C$_{3-7}$cycloalkyl; Ar$^1$; quinolinyl; indolinyl; C$_{1-10}$alkyl; C$_{1-6}$alkyl substituted with Ar$^1$, C$_{3-7}$cycloalkyl, quinolinyl, indolinyl or hydroxy; C$_{1-10}$alkyloxy; C$_{1-6}$alkyloxy substituted with Ar$^1$ or C$_{3-7}$cycloalkyl; C$_{3-6}$alkenyl optionally substituted with Ar$^1$; Ar$^2$-oxy; C$_{1-6}$alkyloxycarbonyl; carboxyl; C$_{1-6}$alkylcarbonyl; Ar$^1$-carbonyl or Ar$^1$—(CHOH)—;

said X being O or S;

said R$^3$ being hydrogen, C$_{1-6}$alkyl or Ar$^2$-C$_{1-6}$alkyl;

Ar$^1$ is phenyl, substituted phenyl, pyridinyl, aminopyridinyl, imidazolyl, thienyl, halothienyl, furanyl, halofuranyl or thiazolyl;

Ar$^2$ is phenyl or substituted phenyl;

in Ar$^1$ and Ar$^2$ said substituted phenyl being phenyl substituted with 1 or 2 substituents each independently selected from halo, hydroxy, trifluoromethyl, C$_{1-6}$alkyl, C$_{1-6}$alkyloxy, cyano, amino, mono- and di(C$_{1-6}$alkyl)amino, nitro, carboxyl, formyl and C$_{1-6}$alkyloxycarbonyl.

20. A method of treating mammals suffering from increased levels of ureic acid, said method comprising the systemic administration to said mammals of an amount effective to treat increased levels of ureic acid of 5-[(1H-imidazol-1-yl)phenylmethyl]-2-methyl-1H-benzimidazole, a pharmaceutically acceptable acid addition salt or a stereochemically isomeric form thereof.

* * * * *

UNITED STATES PATENT AND TRADEMARK OFFICE
CERTIFICATE OF CORRECTION

PATENT NO. : 4,859,684

DATED : Aug. 22, 1989

INVENTOR(S) : Alfons H.M. Raeymaekers, et al.

It is certified that error appears in the above-identified patent and that said Letters Patent is hereby corrected as shown below:

Claim 18, Col. 62, line 53, "$C_{1-10}$ alkyl; $C_{1-6}$ alkyl" should read:

-- $C_{1-10}$ alkyloxy ; $C_{1-6}$ alkyloxy --.

Claim 19, Col. 63, line 38 "$C_{1-1}$ alkyl" should read:

-- $C_{1-10}$ alkyl -- .

Signed and Sealed this

Eleventh Day of September, 1990

*Attest:*

HARRY F. MANBECK, JR.

*Attesting Officer*      *Commissioner of Patents and Trademarks*